(12) United States Patent
Sato

(10) Patent No.: US 6,960,440 B2
(45) Date of Patent: Nov. 1, 2005

(54) METHODS FOR SCREENING FOR APOPTOSIS MODULATORS USING NADE, P75$^{NTR}$-ASSOCIATED CELL DEATH EXECUTOR

(75) Inventor: Taka-Aki Sato, Fort Lee, NJ (US)

(73) Assignee: The Trustes of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/327,750

(22) Filed: Jun. 7, 1999

(65) Prior Publication Data

US 2003/0079237 A1 Apr. 24, 2003

(51) Int. Cl.$^7$ ............... G01N 33/53; G01N 33/567; C12Q 1/68
(52) U.S. Cl. ............... 435/7.1; 435/7.2; 435/6
(58) Field of Search ............... 435/7.1, 7.2, 6, 435/325, 320.1; 536/23.1, 24.33, 24.31, 24.3

(56) References Cited

PUBLICATIONS

Pharmacia Catalog, p. 130, 1994.*
Sambrook, Molecular Cloning Laboratory Manual, 1989, pp. 17.2, 17.25, 17.34, 17.36.*
Hillier et al. Genbank Accession No. N34237, Jan. 1996.*
NCI–CGAP. Genbank Accession No. AA576958, Sep. 1997.*
Rapp et al. Genbank Accession No. M38188, Mar. 1995.*
Lee et al. Genbank Accession No. AI227867, Jan. 1999.*
Brown et al. Genbank Accession No. AF097438, Apr. 1999.*
Faria et al. Genbank Accession No. AF051347, Oct. 1998.*
Brown et al. Genbank Accession No. AF097440, Apr. 1999.*
Marra et al. Genbank Accession No. AI118980, Sep. 1998.*
Marra et al. Genbank Accession No. W46041, May 1996.*
Brown A.L. and Kay G.F., Bex 1, A Gene With Increased Expression In Parthenogenetic Embryos, Is A Member Of A Novel Gene Family On The Mouse X Chromosome, *Human Molecular Genetics* (1999) vol. 8, No. 4, p. 611–619.
Ye X., Mehlen P., Rabizadeh S., VanArsdale T., Zhang H., Shin H., Wang J.J.L., Leo E., Zapata J., Hauser C. A., Reed J.C. and Bredesen D.E., TRAF Family Proteins Interact With The Common Neurotrophin Receptor And Modulate Apoptosis Induction, *The Journal of Biological Chemistry* (1999) vol. 274, No. 42, p. 30202–30208.
Merja S.H. et al., Nerve Growth Factor Signalling Through p75 Induces Apoptosis In Schwann Cells Via A Bcl–2–Independent Pathway, *The Journal of Neuroscience* (1999) vol. 19, p. 4828–4838.
Khursigara G., Orlinick J.R. and Chao M.V., Association Of The p75 Neurotrophin Receptor With TRAF6, *The Journal of Biological Chemistry* (1999) vol. 274, No. 5, p. 2597–2600.

Strausberg R., Nerve Growth Factor Receptor Associated Protein, Database NCBI Online!, May 8, 2002, Database Accession No. BCX027815 XP002234199.
Baeuerle, P.A. & Henkel, T., (1994) Function and Activation of NF–kappa B in the Immune System. *Annu. Rev. Immunol.* 12, 142–179 (Exhibit 1).
Barrett, G. L. & Bartlett, P. F., (1994) The p75 Nerve Growth Factor Receptor Mediates Survival or Death Depending on the Stage of Sensory Neuron Development. *Proc. Natl. Acad. Sci. USA 91*, 6501–6505 (Exhibit 2).
Breeden, L. & Nasmyth, K., (1985) Regulation of the Yeast HO Gene. *Cold Spring Harbor Symp. Quant. Biol.* vol. L, 643, 650 (Exhibit 3).
Bunone, G., Mariotti, A., Compagni, A., Morandi, E. & Della Valle, G., (1997) Induction of Apoptosis by p75 Neurotrophin Receptor in Human Neuroblastoma Cells. *Oncogene 14*, 1463–1470 (Exhibit 4).
Carter, B. D., Kaltschmidt, B., Offenhauser, N., Bohn–Matthaei, R., Baeuerle, P. A. & Barde, Y. A., (1996) Selective Activation of NF–kappa B by Nerve Growth Factor Through the Neurotrophin Receptor p75. *Science 272*, 542–545 (Exhibit 5).
Casaccia–Bonnefil, P., Carter, B. D., Dobrowsky, R. T. & Chao, M. V., (1996) Death of Oligodendrocytes Mediated by the Interaction of Nerve Growth Factor with its Receptor p75. *Nature 383*, 716–719 (Exhibit 6).
Chao, M. V. & Hempstead, B. L., (1995) p75 and Trk: a Two–receptor System. *Trends Neuroscience 18*, 321–326 (Exhibit 7).

(Continued)

*Primary Examiner*—Robert S. Landsman
(74) *Attorney, Agent, or Firm*—John P. White, Esq.; Cooper & Dunham LLP

(57) ABSTRACT

This invention provides an isolated nucleic molecule encoding a polypeptide capable of binding a p75$^{NTR}$ receptor, and a purified version of said polypeptide capable of binding a p75$^{NTR}$ receptor. This invention provides a method of producing a purified polypeptide capable of binding a p75$^{NTR}$ receptor. This invention provides an antisense oligonucleotide having a nucleic acid sequence capable of specifically hybridizing to an mRNA molecule encoding the above described polypeptide. This invention provides a method producing a polypeptide capable of binding p75$^{NT}$ recptor into a suitable vector. This invention provides a method of inducing apoptosis, a method of determining physiological effects, a method for identifying an apoptosis inducing or inhibiting compound, a method for screening cDNA libraries of said polypeptide, a method to induce caspase-2 and caspase-3 activity to cleave poly (ADP-ribose) polymerase and fragment nuclear DNA in a cell, a method to inhibit NF-κB activation in a cell, a method to detect a neurodegenerative disease, a method of producing the isolated human HGR74 protein into a suitable vector, a pharmaceutical composition comprising a purified polypeptide capable of binding a p75$^{NTR}$ receptor and a pharmaceutically acceptable carrier and a method of identifying a compound which is an apoptosis inhibitor.

8 Claims, 16 Drawing Sheets

OTHER PUBLICATIONS

Ciechanover, A., (1998) The Ubiquitin–proteasome Pathway: on Protein Death and Cell Life. *The EMBO Journal* 17(24), 7151–7160 (Exhibit 8).

Datta, R., Banach, D., Kojima, H., Talanian, R. V., Alnemri, E. S., Wong, W. & Kufe, D.W., (1996) Activation of the CPP32 Protease in Apoptosis Induced by 1–beta–D–Arabinofuranosylcytosine and Other DNA–Damaging Agents. *Blood* 88, 1936–1943 (Exhibit 9).

Feinstein, E., Kimchi, A., Wallach, D., Boldin, M. & Varfolomeev, E., (1995) The Death Domain: A Module Shared by Proteins with Diverse Cellular Functions. *Trends Biochem. Sci.* 20, 342–344 (Exhibit 10).

Fernandes–Alnemri, T., Litwack, G. & Alnemri, E. S., (1994) CPP32, a Novel Human Apoptotic Protein with Homology to Caenorhabditis Elegans Cell Death Protein Ced–3 and Mammalian Interleukin–1 Beta–converting Enzyme. *J. Biol. Chem.* 269(49), 30761–30764 (Exhibit 11).

Fields, S. & Song, O., (1989) A Novel Genetic System to Detect Protein–protein Interactions. *Nature* 340, 245–246 (Exhibit 12).

Frade, J. M., Rodriguez–Tebar, A. & Barde, Y.A., (1996) Induction of Cell Death by Endogenous Nerve Growth Factor Through its p75 Receptor. *Nature* 383, 166–168 (Exhibit 13).

Gavrieli, Y., Sherman, Y. & Ben–Sasson, S. A., (1992) Identification of Programmed Cell Death in situ via Specific Labeling of Nuclear DNA Fragmentation. *J. Cell Biol.* 119(3), 493–501 (Exhibit 14).

Gietz, D., Jean, A. S., Woods, R. A. & Schiestl, R. H., (1992) Improved Method for High Efficiency Transformation of Intact Yeast Cells. *Nucl. Acids Res.* 20(6), 1425 (Exhibit 15).

Ito, H., Fukuda, Y., Murata, K. & Kimura, A., (1983) Transformation of Intact Yeast Cells Treated with Alkali Cations. *J. Bacteriol.* 153(1), 163–168 (Exhibit 16).

Johnson, D., Lanathan, A., Buck, C. R., Sehgal, A., Morgan, C., Mercer, E., Bothwell, M. & Chao, M.., (1986) Expression and Structure of the Human NGF Receptor. *Cell* 47, 545–554 (Exhibit 17).

Kaplan, D. R. & Miller, F. D., (1997) Signal Transduction by the Neurotrophin Receptors. *Curr. Opin. Cell Biol.* 9, 213–221 (Exhibit 18).

Khursigara, G., Orlinick, J. R. & Chao, M. V., (1999) Association of the p75 Neurotrophin Receptor with TRAF6 *J. Biol. Chem.* 274(5), 2597–2600 (Exhibit 19).

Lezoualc'h, F., Sagara, Y., Holsboer, F. & Behl, C., (1998) High Constitutive Nf–kappa B Activity Mediates Resistance to Oxidative Stress in Neuronal Cells. *J. Neurosci.* 18(9), 3224–3232 (Exhibit 20).

Liepinsh, E., Ilag, L. L., Otting, G. & Ibanez, C.F., (1997) NMR Structure of the Death Domain of the p75 Neurotrophin Receptor. *The EMBO Journal* 16(16), 4999–5005 (Exhibit 21).

Murphy, T., Cleveland, M., Kulesza, P., Magram, J., Murphy, K., (1995) Regulation of Interleukin 12 p40 Expression through an NF–κB Half–Site. *Molecular and Cellular Biology* 15(10), 5258–5267 (Exhibit 22).

Nakielny, S. & Dreyfuss, G., (1997) Nuclear Export of Proteins and RNAs. *Curr. Opin. Cell Biol.* 9, 420–429 (Exhibit 23).

Pan, J.,McEver, R. P., (1995) Regulation of the Human P–selection Promoter by Bcl–3 and Specific Homodimeric Members of the NF–κB/Rel Family. *J. Biol. Chem.* 270(39), 23077–23083 (Exhibit 24).

Pietravalle, F., Lecoanet–Henchoz, S., Blasey, H., Aubry, J. P., Elson, G., Edgerton, M. D., Bonnefoy, J. Y. & Gauchat, J. F., (1996) Human Native Soluble CD40L is a Biologically Active Trimer, Processed Inside Microsomes. *J. Biol. Chem.* 271(11), 5965–5967 (Exhibit 25).

Rabizadeh, S., Oh, J., Zhong, L., Yang, J., Bitler, C. M., Butcher, L. L. & Bredesen, D. E., (1993) Induction of Apoptosis by the Low–affinity NGF Receptor. *Science* 261, 345–348 (Exhibit 26).

Rapp, G., Freudenstein, J., Klaudiny, J., Mucha, J., Wempe, F., Zimmer, M. & Scheit, K. H., (1990) Characterization of Three Abundant mRNAs from Human Ovarian Granulosa Cells. *DNA and Cell Biol.* 9(7), 479–485 (Exhibit 27).

Schlegel, J., Peters, I., Orrenius, S., Miller, D. K., Thornberry, N. A., Yamin, T. & Nicholson, D. W., (1996) CPP32/Apopain is a Key Interleukin 1 Beta Converting Enzymelike Protease Involved in Fas–mediated Apoptosis. *J. Biol. Chem.* 271(4), 1841–1844 (Exhibit 28).

Schiestl, R. H. & Gist, R. D., (1989) High Efficiency Transformation of Intact Yeast Cells Using Single Stranded Nucleic Acids as a Carrier. *Curr. Genet.* 16, 339–346 (Exhibit 29).

Seilheimer, B., Schachner, M., (1987) Regulation of Neural Cell Adhesion Molecule Expression on Cultured Mouse Schwann Cells by Nerve Growth Factor. *The EMBO Journal.* 6(6), 1611–1616 (Exhibit 30).

Song, W.–J., Tkatch, T., Baranauskas, G., Ichinohe, N., Kitai, S. T., Surmeier, D. J. (1998) Somatodendritic Depolarization–Activated Potassium Currents in Rat Neostriatal Cholinergic Interneurons Are Predominately of the A Type and Attributable to Coexpression of Kv4.2 adn Kv4.1 Subunits. *J. Neurosci.* 18(9), 3124–3137 (Exhibit 31).

Smith, R. A. & Baglioni, C., (1987) The Active Form of Tumor Necrosis Factor Is a Trimer. *J. Biol. Chem.* 262(15), 6951–6954 (Exhibit 32).

Stefanis, L., Troy, C. M., Qi, H., Shelanski, M. L. & Greene, L. A., (1998) Caspase–2 (Nedd–2) Processing and Death of Trophic Factor–Deprived Pc12 Cells and Sympathetic Neurons Occur Independently of Caspase–3 (CPP32)—Like Activity. *J. Neurosci.* 18(22), 9204–9215 (Exhibit 33).

Taglialatela, G., Robinson, R. & Perez–Polo, J.R., (1997) Inhibition of Nuclear Factor Kappa B (NfkappaB) Actively Induces Nerve Growth Factor–Resistant Apoptosis in PC12 Cells. *J. Neurosci. Res.* 47,155–162 (Exhibit 34).

Tanaka, M., Suda, T., Takahashi, T. & Nagata, S., (1995) Expression of the Functional Soluble Form of Human Fas Ligand in Activated Lymphocytes. *The EMBO Journal* 14(6), 1129–1135 (Exhibit 35).

Tewari, M., Quan, L. T., O'Rourke, K., Desnoyers, S., Zeng, Z,. Beidler, D. R., Poirier, G. G., Salvesen, G.S. & Dixit, V. M., (1995) Yama/CPP32beta, A Mammalian Homolog of Ced–3, is a CrnA–Inhibitable Protease that Cleaves the Death Substrate Poly(ADP–Ribose) Polymerase. *Cell* 81, 801–809 (Exhibit 36).

Vojtek, A. B., Hollenberg, S. M. & Cooper, J. A., (1993) Mammalian Ras Interacts Directly with the Serine/Threonine Kinase Raf. *Cell* 74, 205–214 (Exhibit 37).

Weiner, M. P., Felts, K. A., Semcox, T. G. & Braman, J. C., (1993) A Method for the Site–directed Mono– and Multi—mutagenesis of Double–stranded DNA. *Gene* 126, 35–41 (Exhibit 38).

International Search Report (Exhibit B).

Fainzilber M., et al., *CRNF, a Molluscan Neurotrophic Factor That Interacts with the p75 Neurotrophin Receptor,* Science (1996) 274: 1540–1543 (Exhibit C).

Iwane Makoto, et al., *Production, Purification And Characterization Of Biologically Active Recombinant Human Nerve Growth Factor,* Bio. and Biophysical Res. Comm. (1990) 171 (1): 116–122 (Exhibit D).

Mukai, Jun, et al., *Nade, a p75NTR–associated Cell Death Executor, Is Involved in Signal Transduction Mediated by the Common Neurotrophin Receptor p75NTR,* J. of Bio. Chem. (2000) 275 (23): 17566–17570 (Exhibit E).

* cited by examiner

```
Mouse NADE    1  MANVHQENEEMEQPLQNGEEDRPVGGGEGHQPAGNNNNNNHNHHNHHRR
                 |||  ||||||||||| ||||||| ||||||  |||    ||  ||
Human NADE    1  MANIHQENEEMEQPMQNGEEDRPLGGGEGHQPAGN------RR Mouse NADE   51  GQARRLAPNFRWAIPNRQMNDGLGGDDMEMFMEEMREIRKLRELQLR
                 |||||||||||||||||| ||  |||||| |||||||||||||||||
Human NADE   38  GQARRLAPNFRWAIPNRQINDGMGGDDMEIFMEEMREIRKLRELQLR Mouse NADE  101  NCLRILMGELSNHHDHHDEFCLMP  124
                 ||||||||||||| | ||||||||
Human NADE   88  NCLRILMGELSNHHDHHDEFCLMP  111
```

Figure 1A

| | | | | | | | | | | | | | | | |
|---|---|---|---|---|---|---|---|---|---|---|---|---|---|---|---|
| cZyxin | 319-331 | | | | L | T | M | K | E | V | E | E | L | E | L | L | T |
| MAPKK | 32- 44 | | | A | L | Q | K | K | L | E | E | L | E | L | D | E |
| PKI-α | 37- 46 | | | | L | A | L | K | L | A | G | L | D | I | | |
| TFIIIA | 330-338 | | | | | L | P | V | L | E | N | L | T | L | | |
| RevHIV-1 | 73- 81 | | | | | L | P | P | L | E | R | L | T | L | | |
| RanBP1 | 178-189 | | | K | V | A | E | K | L | E | A | L | S | V | R | |
| FMRP | 425-437 | E | V | D | Q | L | R | L | E | R | L | Q | I | D | | |
| Gle1 | 351-356 | | | | | L | P | L | G | K | L | T | L | | | |
| RexHTLV-1 | 81- 94 | | | A | L | S | A | Q | L | Y | S | S | L | S | L | D | S |
| human NADE | 65- 77 | | | R | E | I | R | R | K | L | R | E | L | Q | L | R |
| mouse NADE | 88-100 | | | R | E | I | R | R | K | L | R | E | L | Q | L | R |

Figure 1B

```
                           Box 1              Box 2
Mouse   88-114   REIRRKLRELQLRNCLRILMGELSNHH
Human   75-101   REIRRKLRELQLRNCLRILMGELSNHH
Consensus        RXXLXXLX--N    RXXLXXLXN
```

Mouse

```
  1  acgagcgtctggccagcagctcggagctccttcgcgcgcggcgggctggcagcgggcccg   60
 61  aggcgagcgggacagattgactggaagccgagagtccaggcggcagcgggaattgacagg  120
121  aggactacgccgcaagggataggcccagaatagcaaccaggaaacaaaatctcatcatgg  180
181  ccaatgtccaccaggaaaacgaagagctggagcagccctgcagaatggacaggaagacc   240
241  gccctgtgggaggaggtgagggccaccagcctgctgcaaacaacaacaacaaccaca     300
301  accataaccacaaccaccaccgaagaggccaggctcgccgactgccctaacttccgat    360
361  gggccattcccaacaggcagatgaatgacgggttgggtggagatggagatgatatggaaa  420
421  tgttcatggaggagatgagagagatccggagaaagcttagggagctacagctgagaaatt  480
481  gtctacgcatcctatggggagctgtctaaccaccacgatcaccatgatgaattctgcc    540
541  ttatgccttgacttcggtcattccccctgagatccatactgtgactcccgctgtagccc   600
601  ttccctcgcatttcctgacatgcctttaatgacccgtttgtggtgagcctgtgttat    660
661  tccatgccatgtgccaggtgggcttgtgttgccagtga
```

Human

```
  1  acccatccccactcctataccggtcctccattttggtgcctgcaaagctctgggaaag   60
 60  aatcccgggaaacgaaaaatggtgggttgggggaagggaggtaaggggagaaagctgga  120
121  gggaggggcttaattggaggccccgtagaggacgcgcggaacttctaaggtgggaaaaa  180
181  acgaaattaaaaaatcctttgatatcagggctctgaatcctgctggtcagagcaccaagc  240
241  attcagtctctctccttgcctttgtcttacttgtgttcaaagaaaaacaaccagaaaaaa  300
301  aaaatctcatcatggcaaatattcaccaggaaaacgaagagatggagcagcctatgcaga  360
361  atggagaggaagaccgcctttgggaggaggtgaaggccaccagcctgcaggaaatcgac  420
421  ggggacaggctcgccgacttgccctaatttcgatgggccatacccaataggcagatca   480
481  atgatgggatgggtggagatggagatgatatggaaatattcatggaggagatgagagaaa  540
541  ttagaagaaaacttagggagctgcagttgaggaattgtctgcgtatccttatggggagc  600
601  ttcctaatcaccatgaccatcatgatgaattttgccttatgccttgactcctgccattta  660
661  ttatgagattaatactgtgattccgctgttttctttttccttgcattttcctaatatgc  720
721  ctttactgatccgtttgctgtgaaccctatgttatttccatgtgtcaagtgggtctttgtg  780
781  ttgccagcttctatttgaagatttccttgcactcagtgtaagttcctgtcagcagtagt  840
841  ttcacccattgcatggaaaaatttaaagcgataaagcaatttaaaaaagc
```

Figure 1G-2

```
                      1              15 16             30 31             45 46             60 61             75 76             90
 1 musnade3a  MESKD-QGVKNLNME NDHQKKEEKEEKP-QDTIRREPAVALISEAG KNCAPR------GGRRRFRVR QPIAHYRWDLMQRVG EPQGRMREENVQRFG
 2 hunade3a1  MESKEERALANNLIVE NVNQENDEKDEKE-QVANKGEPL-ALPLNVS EYCVPR------GNRRRFRVR QPILQYRWDIMHRLG EPQARMREENMERIG
 3 hunade3a2  MESKEKRAVNSLSME NANQEN---EEKE-QVANKGEPL-ALPLDAG EYCVPR------GNRRRFPVR QPILQYRWDIMHRLG EPQARMREENMERIG
 4 ratnad3a   MESKD-QGAKNLNME NDHQKKEEKEEKP-QDTIKREPVVAPTFEAG KNCAPR------GGRRRFRVR QPISHYRWDLMHRVG EPQGRMREENVQRFG
 5 ratnad3b   MASKVKQVILDLTVE KDKKNKKGGKASK-QSEEES----HHLEEVEN KKP---------GGNVRRKVR RLVPNFLWAIPNRHV D------HSEGGEEVG
 6 musnade3b  MASKFKQVILDLTVE KDKKDKRGGKASK-QSEEEP----HHLEEVEN KKP---------GGNVRRKVR RLVPNFLWAIPNRHV D------RNEGGEDVG
 7 hunade1              MA NITHQENEEMEQPM-QNGEEDRPLGGGEGHQPA -----------GNRRGQAR RLAPNFRWAIPNRQI N---DGMGGDGDDME
 8 ratnade1               MEQPL-QNGQEDRPVGGGEGHQPAAANNNNHNHNHSHNHNHRRGQAR RLAPNFRWAIPNRQM N---DGLGGDGDDME
 9 musnade1             MA NVHQENEENEQPL-QNGQEDRPVGGGEGHQPAANNNNNHNHNHNHH------RRGQAR RLAPNFRWAIPNRQM N---DGLGGDGDDME
10 hummade2             ME NVPKENKVVEKAPVQN--EAPALGGGEYQEP -------------GGNVKGVWA PPAPGFGEDVPNRLV D-NIDMIDGDGDDME Page 2.1
                     91             105 106            120 121            135 136            150 151            165 166           180
 1 musnade3a  GDMRQLME---KLRE RQLSHSLRAVSTDPP- HHDHHDEFCLMP      130
 2 hunade3a1  EEVRQLME---KLRE KQLSHSLRAVSTDPP -HHDHHDEFCLMP
 3 hunade3a2  EEVRQLME---KLRE KQLSHSLRAVSTDPP -HHDHHDEFCLMP      125
 4 ratnad3a   EDMRQLME---KLRE RQLSHSLRAVSTDPP -HHDHHDEFCLMP
 5 ratnad3b   RFVGQVMEAKRKSKE QQMRPYTRFRTPEPD NHYD----FCLIP
 6 musnade3b  RFVVQGTEVRKRTYE QQVRPYRRFRTPEPD NHYD----FCLIP     97
 7 hunade1    IFMEEMREIRRKLRE LQLRNCLRILMGELS NHHDHHDEFCLMP
 8 ratnade1   MFMEEMREIRRKLRE LQLRNCLRILMGELS NHHDHHDEFCLMP
 9 musnade1   MFMEEMREIRRKLRE LQLRNCLRILMGELS NHHDHHDEFCLMP
10 hummade2   REMEEMRELRRKIRE LQLRYSLRILIGDPP -HHDHHDEFCLMP
```

Figure 1H

Control

NADE p75$^{NTR}$

NADE + p75$^{NTR}$

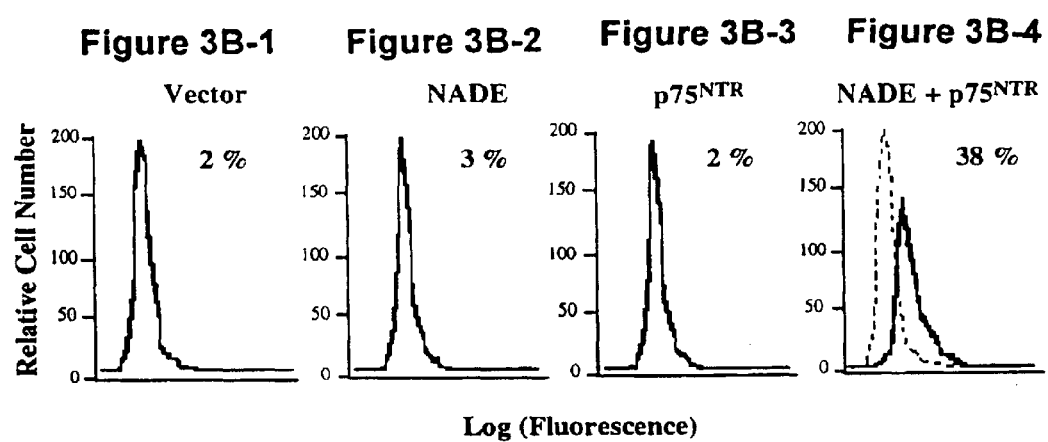

WT mouse NADE-GFP

METHODS FOR SCREENING FOR APOPTOSIS MODULATORS USING NADE, P75$^{NTR}$-ASSOCIATED CELL DEATH EXECUTOR

This invention described herein was supported by National Institutes of Health grant R01-GM55147. Accordingly, the United States Government has certain rights in this invention.

Throughout this application various publications are referred to within parenthesis. Full citations for these publications may be found at the end of the specification immediately preceding the claims. The disclosures of these publications, in their entireties, are hereby incorporated by reference into this application in order to more fully describe the state of the art to which this invention pertains.

BACKGROUND OF THE INVENTION

The low-affinity neurotrophin receptor (p75$^{NTR}$) can mediate cell survival or cell death by NGF or another neurotrophin stimulation in neuronal cells (1, 2, 3) To elucidate p75$^{NTR}$-mediated signal transduction, the yeast two-hybrid system was employed to screen the mouse embryo cDNA libraries using the rat p75$^{NTR}$ICD (intracellular domain) as a target. One positive clone was identified and termed NADE (p75$^{NTR}$-associated cell death executor). This isolated mouse NADE has a significant homology to human HGR74 protein (4) and does not have a typical biochemical motif except the consensus sequences of nuclear export signal (NES) (5) and ubiquitination (6). Expression of NADE mRNA was found highest in the brain, heart, and lung. NADE specifically binds to p75$^{NTR}$ICD both in vitro and in vivo. Co-expression of NADE together with p75$^{NTR}$ dramatically induced Caspase-2 and Caspase-3 activities to clave PARP (poly (ADP-ribose) polymerase) and fragmentation of nuclear DNA in 293T cells, but NADE without p75$^{NTR}$ did not show apoptosis suggesting that NADE expression is necessary for p75$^{NTR}$ mediated apoptosis but is not sufficient to trigger apoptosis. Moreover, NGF dependent recruitment of NADE to p75$^{NTR}$ICD was observed in a dose dependent manner and NADE significantly inhibits NF-kB activation. Interestingly, NADE protein is found to be ubiquitinated as a substrate for protein degradation pathway. Taken together, NADE is the first signal adaptor molecule identified in involvement of p75$^{NTR}$-mediated apoptosis, and it may play an important role in the pathogenes is of neurogenetic disease.

SUMMARY OF THE INVENTION

This invention provides an isolated nucleic molecule encoding a polypeptide capable of binding a p75$^{NTR}$ receptor.

This invention provides a method of producing a polypeptide capable of binding a p75$^{NTR}$ receptor which comprises growing host cells selected from a group consisting of bacterial, plant, insect or mammalian cell, under suitable conditions permitting production of the polypeptide.

This invention provides an antisense oligonucleotide having a nucleic acid sequence capable of specifically hybridizing to an mRNA molecule encoding a polypeptide capable of binding a p75$^{NTR}$ receptor.

This invention provides a purified polypeptide capable of binding a p75$^{NTR}$ receptor.

This invention provides a method of producing a polypeptide capable of binding a p75$^{NTR}$ receptor into a suitable vector which comprises: (a) inserting a nucleic acid molecule encoding the polypeptide capable of binding a p75$^{NTR}$ receptor into a suitable vector; (b) introducing the resulting vector into a suitable host cell; (c) selecting the introduced host cell for the expression of the polypeptide capable of binding a p75$^{NTR}$ receptor; (d) culturing the selected cell to produce the polypeptide capable of binding a p75$^{NTR}$ receptor; and (e) recovering the polypeptide capable of binding a p75$^{NTR}$ receptor produced.

This invention provides a method of identifying a compound capable of inhibiting binding between p75$^{NTR}$ receptor and a polypeptide capable of binding p75$^{NTR}$ receptor, where said binding forms a complex between p75$^{NTR}$ receptor and a polypeptide capable of binding p75$^{NTR}$ receptor, comprising: a) contacting the compound under conditions permitting the binding of the polypeptide capable of binding p75$^{NTR}$ receptor and p75$^{NTR}$ receptor with the polypeptide capable of binding p75$^{NTR}$ receptor to form a mixture; b) contacting p75$^{NTR}$ receptor with the mixture from step a); and c) measuring the amount of complexed p75$^{NTR}$ receptor and a polypeptide capable of binding p75$^{NTR}$ receptor.

This invention provides a method of identifying a compound capable of inhibiting binding between p75$^{NTR}$ receptor and a polypeptide capable of binding p75$^{NTR}$ receptor, where said binding forms a complex between p75$^{NTR}$ receptor and a polypeptide capable of binding p75$^{NTR}$ receptor, comprising: a) contacting the compound under conditions permitting the binding of the polypeptide capable of binding p75$^{NTR}$ receptor and p75$^{NTR}$ receptor with the p75$^{NTR}$ receptor to form a mixture; b) contacting the polypeptide capable of binding a p75$^{NTR}$ receptor with the mixture from step a); and c) measuring the amount of complexed p75$^{NTR}$ receptor and a polypeptide.

This invention provides a method of inducing apoptosis in cells which comprises expressing a polypeptide capable of binding a p75$^{NTR}$ receptor in the cells.

This invention provides a method of inducing apoptosis in a subject which comprises expressing a polypeptide capable of binding a p75$^{NTR}$ receptor in the subject.

This invention provides a method of determining physiological effects of expressing varying levels of a polypeptide capable of binding a p75$^{NTR}$ receptor in a transgenic non-human mammal which comprises producing a panel of transgenic nonhuman mammals, each nonhuman mammal expressing a different amount of polypeptide capable of binding a p75$^{NTR}$ receptor.

This invention provides a method of inducing apoptosis of cells in a subject comprising administering to the subject the purified polypeptide capable of binding a p75$^{NTR}$ receptor in an amount effective to induce apoptosis.

This invention provides a method for identifying an apoptosis inducing compound comprising: (a) contacting a subject with an appropriate amount of the compound; and (b) measuring the expression level of a polypeptide capable of binding a p75$^{NTR}$ receptor gene and p75$^{NTR}$ gene in the subject, an increase of the expression levels of the polypeptide capable of binding a p75$^{NTR}$ receptor gene and p75$^{NTR}$ gene indicating that the compound is an apoptosis inducing compound.

This invention provides a method for identifying an apoptosis inducing compound comprising: (a) contacting a cell with an appropriate amount of the compound; and (b) measuring the expression level of a polypeptide capable of binding a p75$^{NTR}$ receptor gene and p75$^{NTR}$ gene in the cell, an increase of the expression levels of the polypeptide capable of binding a p75$^{NTR}$ receptor and p75$^{NTR}$ gene indicating that the compound is an apoptosis inducing compound.

This invention provides a method for screening cDNA libraries of a polypeptide capable of binding a $p75^{NTR}$ receptor sequence using a yeast two-hybrid system and using a $p75^{NTR}$ intracellular domain as a target.

This invention provides a method to induce caspase-2 and caspase-3 activity to cleave poly (ADP-ribose) polymerase and fragment nuclear DNA in a cell by co-expression of a polypeptide capable of binding a $p75^{NTR}$ receptor and $p75^{NTR}$.

This invention provides a method to inhibit NF-κB activation in a cell with a polypeptide capable of binding a $p75^{NTR}$ receptor and $p75^{NTR}$.

This invention provides a method to detect a neurodegenerative disease in a subject by detecting expression levels of a polypeptide capable of binding a $p75^{NTR}$ receptor and $p75^{NTR}$.

This invention provides a transgenic nonhuman mammal which comprises an isolated nucleic acid, encoding a human HGR74 protein, which is a DNA molecule.

This invention provides a method of determining physiological effects of expressing varying levels of a human HGR74 protein in a transgenic nonhuman mammal which comprises producing a panel of transgenic nonhuman mammal, each nonhuman mammal expressing a different amount of human HGR74 protein.

This invention provides a method of producing the isolated human HGR74 protein into a suitable vector which comprises: (a) inserting a nucleic acid molecule encoding a human HGR74 protein into a suitable vector; (b) introducing the resulting vector into a suitable host cell; (c) selecting the introduced host cell for the expression of the human HGR74 protein; (d) culturing the selected cell to produce the human HGR74 protein; and (e) recovering the human HGR74 protein produced.

This invention provides a method of inducing apoptosis of cells in a subject comprising administering to the subject the purified human HGR74 protein in an amount effective to induce apoptosis.

This invention provides a pharmaceutical composition comprising a purified polypeptide capable of binding a $p75^{NTR}$ receptor and a pharmaceutically acceptable carrier.

This invention provides a method for identifying an apoptosis inducing compound comprising: (a) contacting a subject with an appropriate amount of the compound; and (b) measuring the expression level of human HGR74 protein gene and $p75^{NTR}$ gene in the subject, an increase of the expression levels of human HGR74 protein gene and $p75^{NTR}$ gene indicating that the compound is an apoptosis inducing compound.

This invention provides a method for identifying an apoptosis inducing compound comprising: (a) contacting a cell with an appropriate amount of the compound; and (b) measuring the expression level of human HGR74 gene and $p75^{NTR}$ gene in the cell, an increase of the expression levels of human HGR74 protein gene and $p75^{NTR}$ gene indicating that the compound is an apoptosis inducing compound.

This invention provides a method for screening cDNA libraries human HGR74 sequence using a yeast two-hybrid system using a $p75^{NTR}$ intracellular domain as a target.

This invention provides a method to induce caspase-2 and caspase-3 activity to cleave poly (ADP-ribose) polymerase and fragment nuclear DNA in a cell by co-expression of human HGR74 protein and $p75^{NTR}$.

This invention provides a method to inhibit NF-κB activation in a cell with human HGR74 protein and $p75^{NTR}$.

This invention provides a method to detect a neurodegenerative disease in a subject by detecting expression levels of a polypeptide capable of binding a $p75^{NTR}$ receptor and $p75^{NTR}$.

This invention provides a method of identifying a compound, which is an apoptosis inhibitor, said compound is capable of inhibiting specific binding between a polypeptide capable of binding a $p75^{NTR}$ receptor and $p75^{NTR}$ receptor, so as to prevent apoptosis which comprises: (a) contacting the polypeptide capable of binding a $p75^{NTR}$ receptor with a plurality of compounds under conditions permitting binding between a known compound previously shown to be able to displace the polypeptide capable of binding a $p75^{NTR}$ receptor and the $p75^{NTR}$ receptor and the bound $p75^{NTR}$ receptor to form a complex; and (b) detecting the displaced polypeptide capable of binding a $p75^{NTR}$ receptor or the complex formed in step (a), wherein the displacement indicates that the compound is capable of inhibiting specific binding between the polypeptide capable of binding a $p75^{NTR}$ receptor and the $p75^{NTR}$ receptor.

This invention provides a method of identifying a compound, which is an apoptosis inhibitor, said compound is capable of inhibiting specific binding between human HGR74 protein and $p75^{NTR}$ receptor, so as to prevent apoptosis which comprises: (a) contacting the human HGR74 protein with a plurality of compounds under conditions permitting binding between a known compound previously shown to be able to displace the human HGR74 protein and the $p75^{NTR}$ receptor and the bound $p75^{NTR}$ receptor to form a complex; and (b) detecting the displaced human HGR74 protein or the complex formed in step (a), wherein the displacement indicates that the compound is capable of inhibiting specific binding between the human HGR74 protein and the $p75^{NTR}$ receptor.

BRIEF DESCRIPTION OF FIGURES

The following standard abbreviations are used throughout the specification to indicate specific nucleotides:

C=cytosine
A=adenosine
T=thymidine
G=guanosine

As used herein, amino acid residues are abbreviated as follows:

A=Alanine
C=Cysteine
D=Aspartic Acid
E=Glutamic Acid
F=Phenylalanine
G=Glycine
H=Histidine
I=Isoleucine
K=Lysine
L=Leucine
M=Methionine
N=Asparagine
P=Proline
Q=Glutamine
R=Arginine
S=Serine
T=Threonine
V=Valine
W=Tryptophan
Y=Tyrosine Figure Legends FIG. 1A–H Amino acid sequence and expression analysis of NADE.

FIG. 1A

Amino acid alignment of mouse (SEQ. ID NO:12) and human NADE (HGR74) (4) proteins (SEQ. ID NO:13). The dotted sequence is asparagine rich stretch. The asterisks indicate the leucine-rich nuclear export signal (NES) (5). The closed triangle indicates cysteine residue essential for dimer formation. The prenylation sequence in C-termini is underlined.

FIG. 1B

Comparison of leucine-rich nuclear export signal (NES) (5) in various protein. The consensus sequence for NES are shadowed. Genbank accession numbers are: cZyxin, X69190 (SEQ. ID NO:14); MAPKK, D13700 (SEQ. ID NO:15); PKI-a, L02615 (SEQ. ID NO:16); TFIIIA, M85211 (SEQ. ID NO:17); RevHIV-1, AF075719 (SEQ. ID NO:18); RanBP1, L25255 (SEQ. ID NO:19); FMRP, L29074 (SEQ. ID NO:20); Gle1, U68475 (SEQ. ID NO:21); RexHTLV-1 ((SEQ. ID NO:22); Human NADE (SEQ. ID NO:23), submitted; mouse NADE (SEQ. ID NO:24), submitted.

FIG. 1C

Consensus sequence of ubiquitination signal, Mouse (SEQ. ID NO:25); Human (SEQ. ID NO:26) and Consensus (SEQ. ID NO:27).

FIG. 1D

Northern blot analysis of NADE.

FIG. 1E

Expression of endogenous NADE protein in SK-N-MC human neuroblastoma cells. SK-N-MC cell lysate treated with ALLN is immunoprecipitated by anti-NADE antibody, and subjected to immunoblotting by same antibody. Human NADE protein transiently expressed in 293T cells and untreated gels were used for controls. Heavy chain bands are resulted from antibodies using immunoprecipitation.

FIG. 1F

Mutant analysis of mouse NADE protein A wild type NADE, muNADE(Cys102Ser), and muNADE(Cys121Ser) proteins transiently expressed in 293T cells were detected by immunoblotting with anti-NADE antibody. Transfection methods are described in material and methods. The cell lysate extracted from the 293T cells transfected with parental vector was used as a control.

FIGS. 1G-1 and 1G-2

Blast Search and comparison of mouse NADE nucleic acid sequence FIG. 1G-1 (SEQ ID NO:28) and human protein HGR74 sequence (SEQ. ID NO:29).

FIG. 1H

Comparison of mouse NADE, human HGR74 protein and other homologous rat, mouse and human amino acid sequences: musnade3a (SEQ. ID NO:30); hunade3a1 (SEQ. ID NO:31); hunade3a2 (SEQ. ID NO:32); ratnad3a (SEQ. ID NO:33); ratnad3b (SEQ. ID NO:34); musnade3b (SEQ. ID NO:35); humnade1 (SEQ. ID NO:36); ratnade1 (SEQ. ID NO:37); musnade1 (SEQ. ID NO:38); humnade2 (SEQ. ID NO:39).

Figure 2A:
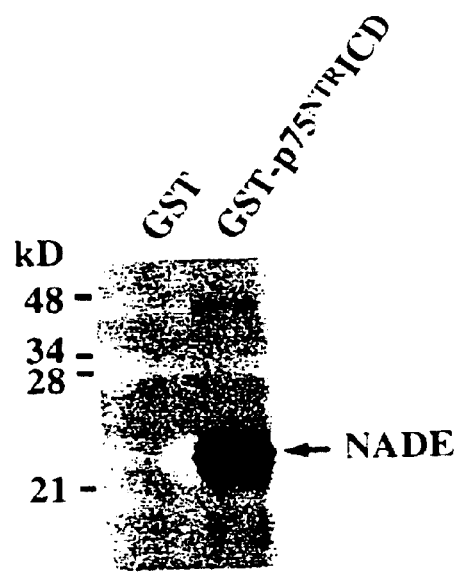
Figure 2B:
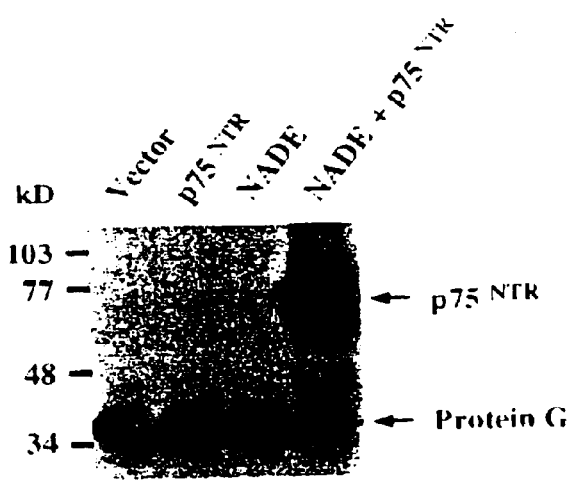
Figure 2C:
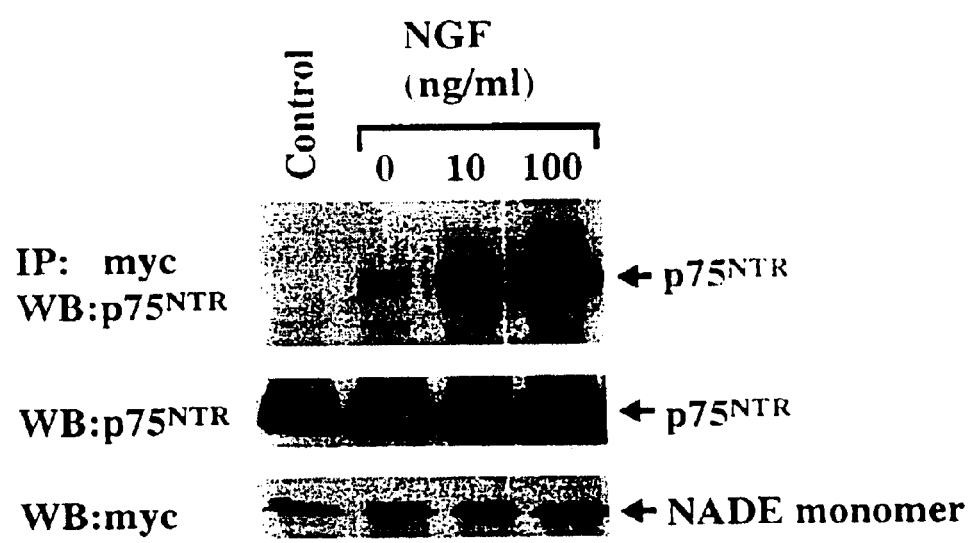

FIG. 2A–C NADE binds to p75$^{NTR}$ strongly in vitro and in vivo.

FIG. 2A

In vitro binding assay of NADE and p75$^{NTR}$. In vitro-translated NADE protein was subjected to GST-pull down assay using a GST-p75$^{NTR}$ICD fusion protein. GST was used as a control.

FIG. 2B

In vivo binding assay of NADE and p75$^{NTR}$. The cell lysates extracted from 293T cells co-transfected with Myc-tagged NADE and p75$^{NTR}$ were co-immunoprecipitated by anti-Myc antibody, and subjected to immunoblotting by anti-p75$^{NTR}$ antibody. The lysates from the cells transfected with each plasmid and a parental vector were used as controls. Transfection methods are described in material and methods.

FIG. 2C

Interaction of NADE with p75$^{NTR}$ depending on NGF ligation. 293T cells co-transfected with Myc-tagged NADE and p75$^{NTR}$ were treated with NGF in various concentration as indicated. Upper panel; Immunoprecipitates of anti-Myc antibody (IgG1) from each sample were subjected to immunoblotting analysis by anti p75$^{NTR}$ antibody. Middle and lower panels indicated the expression level of p75$^{NTR}$ and NADE proteins by immunoblotting, respectively. The immunoprecipitate of anti-FLAG antibody (IgG1) was used as a control.

FIG. 3A–E Effect of NADE and p75$^{NTR}$ co-transfection on 293T cells.

FIG. 3A

Morphological change caused by co-transfection of NADE and p75$^{NTR}$ in 293T cells transfected by each cDNA were observed 48 hours after transfection. The magnification was 200. Transfection methods are described in material and methods.

FIG. 3B

TUNEL assay. Transfected 293T cells were stained by TUNEL method and analyzed by a flow cytometer. The percentages indicated are positive populations.

FIG. 3C

DNA fragmentation analysis. DNAs from transfected 293T cells were checked by 1.5% agarose gel electrophoresis.

FIG. 3D

Inhibition of NF-κB activity by NADE. NF-κB activities in transfected cells were measured by E-selectin promoter-luciferase gene reporter assay. Luciferase activities were determined 24 hours after transfection and normalized on the basis of pRL-TK expression levels.

FIG. 3E

Activation of Caspase-2 and 3 and degradation of PARP in co-transfected 293T cells. The cell extracts from 293T cells transfected by each cDNA as indicated were analyzed by immunoblotting with anti-Caspase-2, Caspase-3, and PAP.P antibody. The level of a-tubulin was measured as a control.

FIG. 4A–D A conserved Rev-like NES in the C-terminus mediates nuclear export of NADE protein.

Figure 4A:
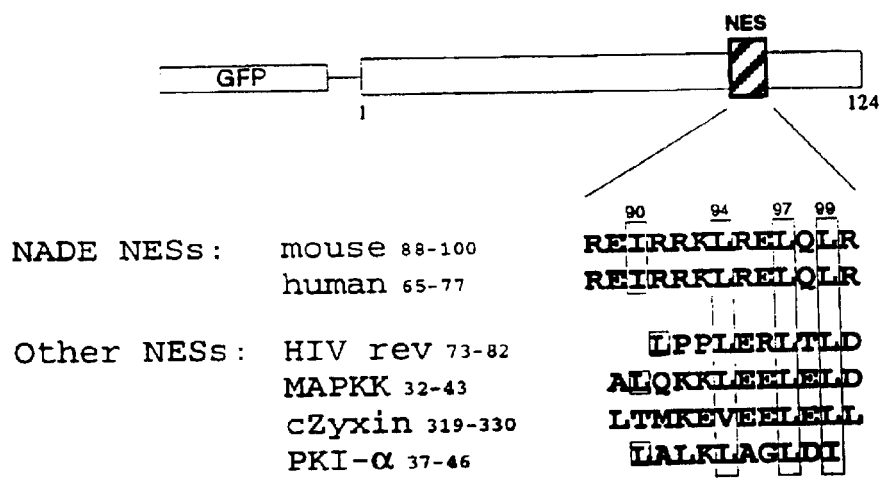
Figure 4B:
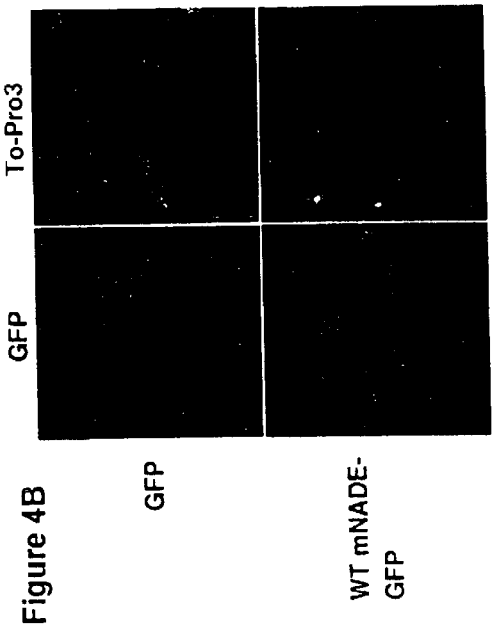
Figure 4D:
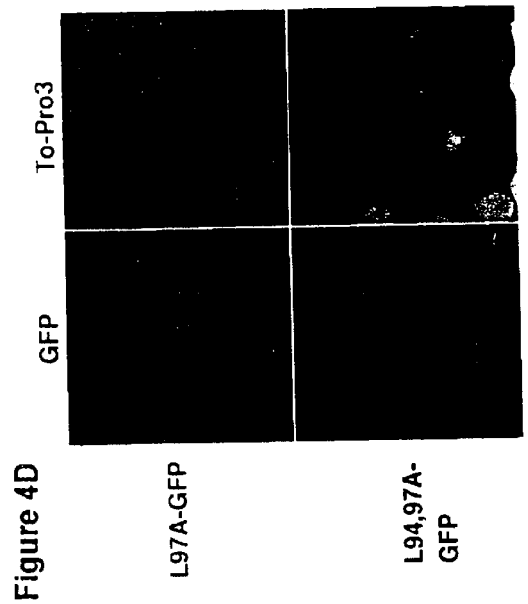
Figure 4C:
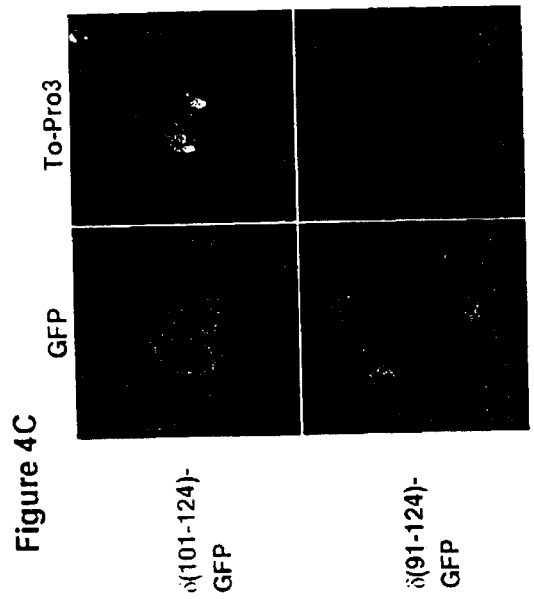

FIG. 4A This invention provides an isolated nucleic molecule encoding a

FIG. 4B

Subcellular localization of a wild type mNADE-GFP and a control GFP vector was analyzed in transfected 293T cells.

FIG. 4C

Effects of deletion mutants of NES motif on nuclear export of GFP-fused mouse NADE proteins. Both deletion mutants with or without NES indicate deletion-124 and delta 91–124, respectively.

FIG. 4D

Effects of point mutations within the NES motif on nuclear export of GFP-fused mouse NADE proteins. The single or double amino acid substitutions were made at residue 94 and 97 (Leu to Ala). GFP-constructs were transiently transfected into 293T cells. The fixed cells were stained with TO-PRO-3 to visualize the nucleus and images of representative cell fields were captured on a confocal laser microscope. More than 1000 cells were analyzed for each construct.

DETAILED DESCRIPTION OF THE INVENTION

The following standard abbreviations are used throughout the specification to indicate specific nucleotides:

C=cytosine
A=adenosine
T=thymidine
G=guanosine

As used herein, amino acid residues are abbreviated as follows:

A=Alanine
C=Cysteine
D=Aspartic Acid
E=Glutamic Acid
F=Phenylalanine
G=Glycine
H=Histidine
I=Isoleucine
K=Lysine
L=Leucine
M=Methionine
N=Asparagine
P=Proline
Q=Glutamine
R=Arginine
S=Serine
T=Threonine
V=Valine
W=Tryptophan
Y=Tyrosine This invention provides an isolated nucleic molecule encoding a polypeptide capable of binding a $p75^{NTR}$ receptor. In an embodiment of the above described isolated nucleic molecule encoding a polypeptide capable of binding a $p75^{NTR}$ receptor the isolated nucleic acid is a DNA molecule. In another embodiment of the above described isolated nucleic acid molecule encoding a polypeptide capable of binding a $p75^{NTR}$ receptor the isolated nucleic acid is a cDNA molecule. In a further embodiment of the above described isolated DNA molecule encoding a polypeptide capable of binding a $p75^{NTR}$ receptor the isolated nucleic acid is a RNA molecule. In an embodiment of the above described isolated nucleic acid molecule encoding a polypeptide capable of binding a $p75^{NTR}$ receptor, the isolated nucleic acid is operatively linked to a promoter of RNA transcription. In yet another embodiment of the above described nucleic acid molecule, said isolated nucleic acid molecule encodes a neurotrophin associated cell death executor protein. In an embodiment of the above described nucleic acid molecule, said isolated nucleic acid molecule comprises a sequence of AATTG TCTAC GCATC CTTAT GGGGG AGCTG TCTAA C (SEQ. ID NO:1).

As used herein, "polypeptide" includes both peptides and proteins. "Peptide" means a polypeptide of fewer than 10 amino acid residues in length, and "protein" means a polypeptide of 10 or more amino acid residues in length. In this invention, the polypeptides may be naturally occurring or recombinant (i.e. produced via recombinant DNA technology), and may contain mutations (e.g. point, insertion and deletion mutations) as well as other covalent modifications (e.g. glycosylation and labeling [via biotin, streptavidin, fluoracine, and radioisotopes such as $^{131}I$]). Moreover, each instant composition may contain more than a single polypeptide, i.e., each may be a monomer (one polypeptide bound to a polymer) or a multimer (two or more polypeptides bound to a polymer or to each other).

The $p75^{NTR}$ receptor is a low affinity nerve growth factor (NGF) receptor with a low affinity to neurotrophins. $p75^{NTR}$ receptor has been implicated in the mediation of cell death and cell survival.

"Capable of binding" is defined as the ability of a protein or other peptide molecule capable of recognizing and interacting with a complementary receptor site, which can be another protein or other type of molecule.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide capable of binding a $p75^{NTR}$ receptor, and as products for the large scale synthesis of the polypeptide capable of binding a $p75^{NTR}$ receptor, or fragments thereof, by a variety of recombinant techniques. The DNA molecule is useful for generating new cloning and expression vectors, transformed and transfected prokaryotic and eukaryotic host cells, and new and useful methods for cultured growth of such host cells capable of expression of the polypeptide capable of binding a $p75^{NTR}$ receptor or portions thereof and related products.

This invention provides a vector which comprises the isolated nucleic acid encoding a polypeptide capable of binding a $p75^{NTR}$ receptor, operatively linked to a promoter of RNA transcription. In an embodiment of the invention, where in the vector which comprises the isolated nucleic acid encoding a polypeptide capable of binding a $p75^{NTR}$ receptor, operatively linked to a promoter of RNA transcription is a plasmid. In another embodiment the above described isolated nucleic acid molecule which is a cDNA molecule encoding a polypeptide capable of binding a $p75^{NTR}$ receptor, encodes a human or mouse protein. In yet another embodiment the above described isolated nucleic acid molecule is a cDNA molecule wherein the nucleic acid molecule encodes a polypeptide capable of binding a $p75^{NTR}$ receptor comprising the amino acid sequence set forth in FIG. 1A (SEQ. ID NO:13). In a further embodiment the above described isolated nucleic acid molecule is a cDNA molecule where,in the nucleic acid molecule encodes a polypeptide capable of binding a $p75^{NTR}$ receptor. In an embodiment of the above described isolated nucleic acid molecule which is a cDNA molecule wherein the nucleic acid molecule encodes a polypeptide capable of binding p75NTR receptor which is a mouse, rat or human protein. In yet another embodiment of the above described isolated nucleic acid molecule which is a cDNA molecule, said isolated nucleic acid molecule comprises the nucleic acid sequence set forth in FIG. 1G-1 (SEQ. ID NO:29).

Numerous vectors for expressing the inventive proteins may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The markers may provide, for example, prototrophy to an auxotrophic host, biocide resistance or resistance to heavy metals such as copper. The selectable marker gene can be either directly linked to the DNA sequences to be expressed, or introduced into the same cell by cotransformation.

Regulatory elements required for expression include promoter sequences to bind RNA polymerase and transcription initiation sequences for ribosome binding. Additional elements may also be needed for optimal synthesis of mRNA. These additional elements may include splice signals, as well as enhancers and termination signals. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general.

These vectors may be introduced into a suitable host cell to form a host vector system for producing the inventive proteins. Methods of making host vector systems are well known to those skilled in the art.

Methods of introducing nucleic acid molecules into cells are well known to those of skill in the art. Such methods include, for example, the use of viral vectors and calcium phosphate co-precipitation.

This invention provides a host cell comprising the vector comprising the nucleic acid molecule of encoding a polypeptide capable of binding $p75^{NTR}$ receptor. In an embodiment the above described host cell is selected from a group consisting of a bacterial cell, a plant cell, and insect cell, and a mammalian cell.

The "suitable host cell" in which the nucleic acid molecule encoding is a polypeptide capable of binding a $p75^{NTR}$ receptor capable of being expressed is any cell capable of taking up the nucleic acid molecule and stably expressing the polypeptide capable of binding a $p75^{NTR}$ receptor encoded thereby.

Suitable host cells include, but are not limited to, bacterial cells (including gram positive cells), yeast cells, fungal cells, insect cells and animal cells. Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk$^-$ cells and COS cells. Mammalian cells may be transfected by methods well known in the art such as calcium phosphate precipitation, electroporation and microinjection.

This invention provides a method of producing a polypeptide having the biological activity of a polypeptide capable of binding a $p75^{NTR}$ receptor which comprises growing host cells selected from a group consisting of bacterial, plant, insect or mammalian cell, under suitable conditions permitting production of the polypeptide. In another embodiment of the above described method of producing a polypeptide having the biological activity of a polypeptide capable of binding a $p75^{NTR}$ receptor, the method further comprises the recovering of the produced polypeptide.

This invention provides an isolated nucleic acid molecule of at least 15 contiguous nucleotides capable of specifically hybridizing with a unique sequence included within the sequence of the nucleic acid molecule encoding a polypeptide capable of binding a $p75^{NTR}$ receptor. In an embodiment of the above described isolated nucleic acid molecule of at least 15 contiguous nucleotides capable of specifically hybridizing with a unique sequence included within the sequence of the nucleic acid molecule encoding a polypeptide capable of binding a $p75^{NTR}$ receptor, said isolated nucleic acid molecule is a DNA molecule. In another embodiment of the above described isolated nucleic acid molecule of at least 15 contiguous nucleotides capable of specifically hybridizing with a unique sequence included within the sequence of the nucleic acid molecule encoding a polypeptide capable of binding a $p75^{NTR}$ receptor, said isolated nucleic acid molecule is a RNA molecule.

This invention provides an isolated nucleic acid molecule capable of specifically hybridizing with a unique sequence included within the sequence of a nucleic acid molecule which is complementary to the nucleic acid molecule encoding a polypeptide capable of binding a $p75^{NTR}$ receptor. In an embodiment the above described isolated nucleic acid molecule which is complementary to the nucleic acid molecule encoding a polypeptide capable of binding a $p75^{NTR}$ receptor is a DNA molecule. In another embodiment the above described isolated nucleic acid molecule capable of specifically hybridizing with a nucleic acid molecule capable of specifically hybridizing with a unique sequence included within the sequence of a nucleic acid molecule which is complementary to the nucleic acid molecule encoding a polypeptide capable of binding a $p75^{NTR}$ receptor is a RNA molecule.

One of ordinary skill in the art will easily obtain unique sequences from the cDNA cloned in the polypeptide capable of binding a $p75^{NTR}$ receptor plasmid. Such unique sequences may be used as probes to screen various mammalian cDNA libraries and genomic DNAs, e.g. mouse, rat and bovine, to obtain homologous nucleic acid sequences and to screen different cDNA tissue libraries to obtain isoforms of the obtained nucleic acid sequences. Nucleic acid probes from the cDNA cloned in the polypeptide capable of binding a $p75^{NTR}$ receptor plasmid may further be used to screen other human tissue cDNA libraries to obtain isoforms of the nucleic acid sequences encoding polypeptide capable of binding a $p75^{NTR}$ receptor as well as to screen human genomic DNA to obtain the analogous nucleic acid sequences. The homologous nucleic acid sequences and isoforms may be used to produce the proteins encoded thereby.

As used herein, "capable of specifically hybridizing" means capable of binding to an mRNA molecule encoding a polypeptide capable of binding a $p75^{NTR}$ receptor but not capable of binding to a polypeptide capable of binding a $p75^{NTR}$ receptor molecule encoding a polypeptide capable of binding a $p75^{NTR}$ receptor.

This invention provides an antisense oligonucleotide having a nucleic acid sequence capable of specifically hybridizing to an mRNA molecule encoding a polypeptide capable of binding a $p75^{NTR}$ receptor. In an embodiment of the above described antisense oligonucleotide, said antisense oligonucleotide has a nucleic acid sequence capable of specifically hybridizing to the isolated cDNA molecule encoding a polypeptide capable of binding a p75$^{NTR}$ receptor. In another embodiment of the above described antisense oligonucleotide has a nucleic acid sequence capable of specifically hybridizing to the isolated RNA molecule encoding a polypeptide capable of binding a p75$^{NTR}$ receptor.

This invention provides a purified a polypeptide capable of binding a p75$^{NTR}$ receptor. In an embodiment of the above described purified polypeptide capable of binding p75$^{NTR}$ receptor is encoded by the isolated nucleic acid encoding a polypeptide capable of binding a p75$^{NTR}$ receptor. In an embodiment the above described polypeptide capable of binding a p75$^{NTR}$ receptor is a fragment of the purified polypeptide capable of binding a receptor. In another embodiment the above described purified polypeptide capable of binding a p75$^{NTR}$ receptor has substantially the same amino acid sequence as set forth in FIG. 1A (SEQ. ID NO:13). In a further embodiment the above described purified polypeptide capable of binding a p75$^{NTR}$ receptor having an amino acid sequence as set forth in FIG. 1A (SEQ. ID NO:13). In yet another embodiment the above described polypeptide capable of binding a p75$^{NTR}$ receptor has an amino acid sequence as set forth in FIG. 1A (SEQ. ID NO:13). In a further embodiment, the above described polypeptide capable of binding a p75$^{NTR}$ receptor is a vertebrate polypeptide capable of binding a p75$^{NTR}$ receptor. In an embodiment of the above described polypeptide capable of binding a p75$^{NTR}$ receptor comprises a neurotrophin associated cell death executor protein. In yet another embodiment of the above described polypeptide capable of binding a p75$^{NTR}$ receptor comprises NCLRILMGELSN (SEQ. ID NO:2).

As used herein, purified polypeptides means the polypeptides free of any other polypeptides.

As used herein, a polypeptide capable of binding a p75$^{NTR}$ receptor having "substantially the same" amino acid sequences as set forth in FIG. 1A (SEQ ID NO:13) is encoded by a nucleic acid encoding a polypeptide capable of binding a p75$^{NTR}$ receptor, said nucleic acid having 100% identity in the homeodomain regions, that is those regions coding the protein, and said nucleic acid may vary in the nucleotides in the non-coding regions.

This invention provides a monoclonal antibody directed to an epitope of a polypeptide capable of binding a p75$^{NTR}$ receptor. In an embodiment the above described monoclonal antibody, said monoclonal antibody is directed to a mouse, rat or human polypeptide capable of binding a p75$^{NTR}$ receptor.

The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies, wholly synthetic antibodies, and fragments thereof. Optionally, an antibody can be labeled with a detectable marker. Detectable markers include, for example, radioactive or fluorescent markers.

This invention provides a polyclonal antibody directed to an epitope of the purified protein having the amino sequence as set forth in FIG. 1A (SEQ ID NO:13). In a further embodiment the above described monoclonal or polyclonal antibodies are directed to the polypeptide capable of binding a p75$^{NTR}$ receptor, having the amino sequence as set forth in FIG. 1A (SEQ ID NO:13).

Polyclonal antibodies may be produced by injecting a host animal such as rabbit, rat, goat, mouse or other animal with the immunogen of this invention, e.g. a purified mammalian polypeptide capable of binding a p75$^{NTR}$ receptor or a purified human polypeptide capable of binding a p75$^{NTR}$ receptor. The sera are extracted from the host animal and are screened to obtain polyclonal antibodies which are specific to the immunogen. Methods of screening for polyclonal antibodies are well known to those of ordinary skill in the art such as those disclosed in Harlow & Lane, *Antibodies: A Laboratory Manual*, (Cold Spring Harbor Laboratories, Cold Spring Harbor, N.Y.: 1988) the contents of which are hereby incorporated by reference.

The monoclonal antibodies may be produced by immunizing for example, mice with an immunogen. The mice are inoculated intra-peritoneally with an immunogenic amount of the above-described immunogen and then boosted with similar amounts of the immunogen. Spleens are collected from the immunized mice a few days after the final boost and a cell suspension is prepared from the spleens for use in the fusion.

In the practice of the subject invention any of the above-described antibodies may be labeled with a detectable marker. In one embodiment, the labeled antibody is a purified labeled antibody. As used in the subject invention, the term "antibody" includes, but is not limited to, both naturally occurring and non-naturally occurring antibodies. Specifically, the term "antibody" includes polyclonal and monoclonal antibodies, and binding fragments thereof. Furthermore, the term "antibody" includes chimeric antibodies and wholly synthetic antibodies, and fragments thereof.

Furthermore, the term "antibody" includes chimeric antibodies and wholly synthetic antibodies, and fragments thereof. A "detectable moiety" which functions as detectable labels are well known to those of ordinary skill in the art and include, but are not limited to, a fluorescent label, a radioactive atom, a paramagnetic ion, biotin, a chemiluminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin. Methods of labeling antibodies are well known in the art.

Determining whether the antibody forms such a complex may be accomplished according to methods well known to those skilled in the art. In the preferred embodiment, the determining is accomplished according to flow cytometry methods.

The antibody may be bound to an insoluble matrix such as that used in affinity chromatography. As used in the subject invention, isolating the cells which form a complex with the immobilized monoclonal antibody may be achieved by standard methods well known to those skilled in the art. For example, isolating may comprise affinity chromatography using immobilized antibody.

Alternatively, the antibody may be a free antibody. In this case, isolating may comprise cell sorting using free, labeled primary or secondary antibodies. Such cell sorting methods are standard and are well known to those skilled in the art.

The labeled antibody may be a polyclonal or monoclonal antibody. In one embodiment, the labeled antibody is a purified labeled antibody. The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. The detectable marker may be, for example, radioactive or fluorescent. Methods of labeling antibodies are well known in the art.

This invention provides a method of inducing apoptosis in cells which comprises expressing polypeptide capable of binding a $p75^{NTR}$ receptor in the cells.

This invention provides a method of inducing apoptosis in a subject which comprises expressing a polypeptide capable of binding a $p75^{NTR}$ receptor in the subject. In a further embodiment of the method of inducing apoptosis in a subject where the subject is a rat, mouse or human.

As used herein, "subject" means any animal or artificially modified animal. Artificially modified animals include, but are not limited to, SCID mice with human immune systems. In the preferred embodiment, the subject is a human.

This invention provides a transgenic nonhuman mammal which comprises an isolated nucleic acid, encoding a polypeptide capable of binding a $p75^{NTR}$ receptor, which is a DNA molecule. In an embodiment of the above described transgenic nonhuman mammal, the DNA encoding a polypeptide capable of binding a $p75^{NTR}$ receptor is operatively linked to tissue specific regulatory elements.

This invention provides a method of determining physiological effects of expressing varying levels of a polypeptide capable of binding a $p75^{NTR}$ receptor in a transgenic nonhuman mammal which comprises producing a panel of transgenic nonhuman mammals, each nonhuman mammal expressing a different amount of a polypeptide capable of binding a $p75^{NTR}$ receptor.

This invention provides a method of producing a polypeptide capable of binding a $p75^{NTR}$ receptor into a suitable vector which comprises: (a) inserting a nucleic acid molecule encoding the polypeptide capable of binding a $p75^{NTR}$ receptor into a suitable vector; (b) introducing the resulting vector into a suitable host cell; (c) selecting the introduced host cell for the expression of the polypeptide capable of binding a $p75^{NTR}$ receptor; (d) culturing the selected cell to produce the polypeptide capable of binding a $p75^{NTR}$ receptor; and (e) recovering the polypeptide capable of binding a $p75^{NTR}$ receptor produced.

This invention provides a method of inducing apoptosis of cells in a subject comprising administering to the subject the purified polypeptide capable of binding a $p75^{NTR}$ receptor in an amount effective to induce apoptosis. In an embodiment of the above described method of inducing apoptosis of cells in a subject comprising administering to the subject the purified polypeptide capable of binding a $p75^{NTR}$ receptor in an amount effective to induce apoptosis, the subject is a mammal. In another embodiment of the above-described method of inducing apoptosis of cells in a subject, the subject is a mouse, rat or human.

As used herein "apoptosis" means programmed cell death of the cell. The mechanisms and effects of programmed cell death differs from cell lysis. Some observable effects of apoptosis are: DNA fragmentation and disintegration into small membrane-bound fragments called apoptotic bodies.

As used herein, "subject" means any animal or artificially modified animal. Artificially modified animals include, but are not limited to, SCID mice with human immune systems. In the preferred embodiment, the subject is a human.

This invention provides a pharmaceutical composition comprising a purified polypeptide capable of binding a $p75^{NTR}$ receptor and a pharmaceutically acceptable carrier.

The invention also provides a pharmaceutical composition comprising a effective amount of the polypeptides capable of binding a $p75^{NTR}$ receptor described above and a pharmaceutically acceptable carrier. In the subject invention an "effective amount" is any amount of above-described polypeptides capable of binding a $p75^{NTR}$ receptor which, when administered to a subject suffering from a disease or abnormality against which the proteins are determined to be potentially therapeutic, are effective, causes reduction, remission, or regression of the disease or abnormality. In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The above described pharmaceutical composition comprising a polypeptide capable of binding a p75$^{NTR}$ receptor can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The above described pharmaceutical composition comprising a polypeptide capable of binding a p75$^{NTR}$ receptor can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular above described pharmaceutical composition comprising a polypeptide capable of binding a p75$^{NTR}$ receptor in use, the strength of the preparation, the mode of administration, and the advancement of the disease condition or abnormality. Additional factors depending on the particular subject being treated will result in a need to adjust dosages, including subject age, weight, gender, diet, and time of administration.

As used herein, administering may be effected or performed using any of the various methods known to those skilled in the art. The administration may be intravenous, intraperitoneal, intrathecal, intralymphatical, intramuscular, intralesional, parenteral, epidural, subcutaneous; by infusion, liposome-mediated delivery, aerosol delivery; topical, oral, nasal, anal, ocular or otic delivery.

A method of identifying a compound capable of inhibiting binding between p75$^{NTR}$ receptor and a polypeptide capable of binding p75$^{NTR}$ receptor comprising: a) contacting the compound with the polypeptide capable of binding to p75$^{NTR}$ receptor under conditions permitting the binding of the polypeptide capable of binding to p75$^{NTR}$ receptor and p75$^{NTR}$ receptor to form a complex; b) contacting the p75$^{NTR}$ receptor with the mixture from step a); and c) measuring the amount of the formed complexes or the unbound p75$^{NTR}$ receptor or the unbound polypeptide or any combination thereof. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a neurotrophin associated cell death executor. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a human HGR74 protein. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a musnade3a sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a hunade3a1 sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ a hunade3a2 sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ a ratnad3a sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a ratnad3b sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a musnade3b sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a humnade1 sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a ratnade1 sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a musnade1 sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a humnade2 sequence as defined on FIG. 1H.

A method of identifying a compound capable of inhibiting binding between p75$^{NTR}$ receptor and a polypeptide capable of binding p75$^{NTR}$ receptor, where said binding forms a complex between p75$^{NTR}$ receptor and a polypeptide capable of binding p75$^{NTR}$ receptor, comprising: a) contacting the compound with the p75$^{NTR}$ receptor under conditions permitting the binding of the polypeptide capable of binding to p75$^{NTR}$ receptor and p75$^{NTR}$ receptor to form a complex; b) contacting the p75$^{NTR}$ receptor with the mixture from step a); and c) measuring the amount of the formed complexes or the unbound p75$^{NTR}$ receptor or the unbound polypeptide or any combination thereof.

In an embodiment of the above described method of identifying a compound capable of inhibiting between p75$^{NTR}$ receptor and a polypeptide capable of binding p75$^{NTR}$ where said polypeptide capable of binding p75$^{NTR}$ is a neurotrophin associated cell death executor protein. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a human HGR74 protein. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a musnade3a sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a hunade3a1 sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ a hunade3a2 sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ a ratnad3a sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a ratnad3b sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a musnade3b sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a humnade1 sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a ratnade1 sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a musnade1 sequence as defined on FIG. 1H. In an embodiment of the above described method of identifying a compound capable of inhibiting between p75$^{NTR}$ receptor and a polypeptide capable of binding p75$^{NTR}$ where said polypeptide capable of binding p75$^{NTR}$ is a humnade2 sequence as defined on FIG. 1H.

This invention provides a method for identifying an apoptosis inducing compound comprising: (a) contacting a subject with an appropriate amount of the compound; and (b) measuring the expression level of polypeptide capable of binding a p75$^{NTR}$ receptor gene and p75$^{NTR}$ gene in the subject, an increase of the expression levels of a polypeptide capable of binding a p75$^{NTR}$ receptor gene and p75$^{NTR}$ gene indicating that the compound is an apoptosis inducing compound. In an embodiment of the above described method for identifying an apoptosis inducing compound comprising: a) contacting a subject with an appropriate amount of the compound; and (b) measuring the expression level of polypeptide capable of binding a p75$^{NTR}$ receptor gene and p75$^{NTR}$ gene in the subject, an increase of the expression levels of a polypeptide capable of binding a p75$^{NTR}$ receptor gene and p75$^{NTR}$ gene indicating that the compound is an apoptosis inducing compound, wherein the subject is a mammal. In an embodiment of the above-described method of identifying an apoptosis inducing compound, wherein the mammal subject is a mouse, rat or human.

This invention provides a method for identifying an apoptosis inducing compound comprising: (a) contacting a cell with an appropriate amount of the compound; and (b) measuring the expression level of polypeptide capable of binding a p75$^{NTR}$ receptor gene and p75$^{NTR}$ gene in the cell, an increase of the expression levels of polypeptide capable of binding a p75$^{NTR}$ receptor gene and p75$^{NTR}$ gene indicating that the compound is an apoptosis inducing compound.

An apoptosis inducing compound is defined as a compound which may be, but not limited to, antibodies, inorganic compounds, organic compounds, peptides, peptidomimetic compounds, polypeptides or proteins, fragments or derivatives which share some or all properities, e.g. fusion proteins, that induces apoptosis. The compounds may be naturally occurring and obtained by purification, or may be non-naturally occurring and obtained by synthesis.

This invention provides a method for screening cDNA libraries encoding a polypeptide capable of binding a p75$^{NTR}$ receptor sequence using a yeast two-hybrid system and using a p75$^{NTR}$ intracellular domain as a target. In an embodiment of the above described method for screening cDNA libraries for polypeptide capable of binding a p75$^{NTR}$ receptor sequence using a yeast two-hybrid system and using a p75$^{NTR}$ intracellular domain as a target, where the cDNA library is mammalian. In another embodiment of the above described method for screening cDNA libraries for a polypeptide capable of binding a p75$^{NTR}$ receptor using a yeast two-hybrid system and using a p75$^{NTR}$ intracellular domain as a target, where the cDNA library is mammalian and where the mammalian cDNA library is derived from rat, mouse or human cDNA libraries. In an embodiment of the above described method for screening cDNA libraries for a polypeptide capable of binding a p75$^{NTR}$ receptor, using a yeast two-hybrid system and using a p75$^{NTR}$ intracellular domain as a target, where the p75$^{NTR}$ intracellular domain target is mammalian. In an embodiment of the above described method for screening cDNA libraries for a polypeptide capable of binding a p75$^{NTR}$ receptor using a yeast two-hybrid system and using a p75$^{NTR}$ intracellular domain as a target, where the p75$^{NTR}$ intracellular domain target is a rat, mouse or human p75$^{NTR}$ intracellular domain target.

This invention provides a method to induce caspase-2 and caspase-3 activity to cleave poly (ADP-ribose) polymerase and fragment nuclear DNA in a cell by co-expression of a polypeptide capable of binding a p75$^{NTR}$ receptor and p75$^{NTR}$.

Caspases are members of the protease family, the mammalian homologs of the Caenorhabiditis elegans death gene ced-3, which are required for mammalian apoptosis. Increased levels of caspase-2 and caspase-3 have been linked to apoptosis. The caspases are cysteine aspartases that cleave their substrates at aspartate residues. To activate caspases, they need to be cleaved at aspartate residues and to form active heterodimers.

This invention provides a method to inhibit NF-κB activation in a cell with a polypeptide capable of binding a p75$^{NTR}$ receptor and p75$^{NTR}$.

NF-κB is a primary transcription factor which is activated by external stimuli, and translocated to the nucleus where it binds to DNA and regulates gene transcription. In rat Schwann cells, the binding of nerve growth factor to p75$^{NTR}$ neurotrophin receptor, induces the activation of NF-κB in the absence of tyrosine kinase receptor A, and led to cell survival. NF-κB regulates the gene expression of various proteins including cell surface molecules and cytokines.

This invention provides a method to detect a neurodegenerative disease in a subject by detecting expression levels of a polypeptide capable of binding a p75$^{NTR}$ receptor and p75$^{NTR}$. In an embodiment of the above described method to detect a neurodegenerative disease in a subject by detecting expression levels of a polypeptide capable of binding a p75$^{NTR}$ receptor and p75$^{NTR}$, wherein the subject is a mammal. In another embodiment of the above described method to detect a neurodegenerative disease in a subject by detecting expression levels of a polypeptide capable of binding a p75$^{NTR}$ receptor and p75$^{NTR}$ wherein the mammal subject is mouse, rat or human.

This invention provides a transgenic nonhuman mammal which comprises an isolated nucleic acid, encoding a human HGR74 protein, which is a DNA molecule. In an embodiment of the above described transgenic nonhuman mammal, the DNA encoding a human HGR74 protein is operatively linked to tissue specific regulatory elements.

This invention provides a method of determining physiological effects of expressing varying levels of a human HGR74 protein in a transgenic nonhuman mammal which comprises producing a panel of transgenic nonhuman mammal, each nonhuman mammal expressing a different amount of human HGR74 protein.

This invention provides a method of producing the isolated human HGR74 protein into a suitable vector which comprises: (a) inserting a nucleic acid molecule encoding a human HGR74 protein into a suitable vector; (b) introducing the resulting vector into a suitable host cell; (c) selecting the introduced host cell for the expression of the human HGR74 protein; (d) culturing the selected cell to produce the human HGR74 protein; and (e) recovering the human HGR74 protein produced.

This invention provides a method of inducing apoptosis of cells in a subject comprising administering to the subject the purified human HGR74 protein in an amount effective to induce apoptosis. In an embodiment of the above described method of inducing apoptosis of cells in a subject comprising administering to the subject the purified human HGR74 in an amount effective to induce apoptosis, the subject is a mammal. In another embodiment of the above-described method of inducing apoptosis of cells in a subject, the subject is a mouse, rat or human.

This invention provides a pharmaceutical composition comprising a purified human HGR74 protein and a pharmaceutically acceptable carrier.

This invention provides a method for identifying an apoptosis inducing compound comprising: (a) contacting a subject with an appropriate amount of the compound; and (b) measuring the expression level of human HGR74 protein gene and $p75^{NTR}$ gene in the subject, an increase of the expression levels of human HGR74 protein gene and $p75^{NTR}$ gene indicating that the compound is an apoptosis inducing compound. In an embodiment of the above described method for identifying an apoptosis inducing compound comprising: a) contacting a subject with an appropriate amount of the compound; and (b) measuring the expression level of human HGR74 protein gene and $p75^{NTR}$ gene in the subject, an increase of the expression levels of human HGR74 protein gene and $p75^{NTR}$ gene indicating that the compound is an apoptosis inducing compound, wherein the subject is a mammal. In an embodiment of the above-described method of identifying an apoptosis inducing compound, wherein the mammal subject is a mouse, rat or human.

This invention provides a method for identifying an apoptosis inducing compound comprising: (a) contacting a cell with an appropriate amount of the compound; and (b) measuring the expression level of human HGR74 gene and $p75^{NTR}$ gene in the cell, an increase of the expression levels of human HGR74 protein gene and $p75^{NTR}$ gene indicating that the compound is an apoptosis inducing compound.

This invention provides a method for screening cDNA libraries human HGR74 sequence using a yeast two-hybrid system using a $p75^{NTR}$ intracellular domain as a target. In an embodiment of the above described method for screening cDNA libraries human HGR74 sequence using a yeast two-hybrid system using a $p75^{NTR}$ intracellular domain as a target, where the cDNA library is mammalian. In an embodiment of the above described method for screening cDNA libraries human HGR74 sequence using a yeast two-hybrid system using a $p75^{NTR}$ intracellular domain as a target, where the cDNA library is mammalian and where the mammalian cDNA library is derived from rat, mouse or human cDNA libraries. In another embodiment of the above described method for screening cDNA libraries human HGR74 sequence using a yeast two-hybrid system using a $p75^{NTR}$ intracellular domain as a target, where the $p75^{NTR}$ intracellular domain target is mammalian. In an embodiment of the above described method for screening cDNA libraries human HGR74 sequence using a yeast two-hybrid system using a $p75^{NTR}$ intracellular domain as a target, where the $p75^{NTR}$ intracellular domain target is a rat, mouse or human $p75^{NTR}$ intracellular domain target.

This invention provides a method to induce caspase-2 and caspase-3 activity to cleave poly (ADP-ribose) polymerase and fragment nuclear DNA in a cell by co-expression of human HGR74 protein and $p75^{NTR}$.

This invention provides a method to inhibit NF-KB activation in a cell with human HGR74 protein and $p75^{NTR}$.

This invention provides a method to detect a neurodegenerative disease in a subject by detecting expression levels of polypeptide capable of binding a $p75^{NTR}$ receptor a and $p75^{NTR}$. In an embodiment of the above described method to detect a neurodegenerative disease in a subject by detecting expression levels of polypeptide capable of binding a $p75^{NTR}$ receptor and $p75^{NTR}$, wherein the subject is a mammal. In another embodiment of the above described method to detect a neurodegenerative disease in a subject by detecting expression levels of polypeptide capable of binding a $p75^{NTR}$ receptor and $p75^{NTR}$, wherein the subject is a mammal wherein the mammal is human.

This invention provides a method of identifying a compound, which is an apoptosis inhibitor, said compound is capable of inhibiting specific binding between a polypeptide capable of binding a $p75^{NTR}$ receptor and $p75^{NTR}$ receptor, so as to prevent apoptosis which comprises: (a) contacting the polypeptide capable of binding a $p75^{NTR}$ receptor with a plurality of compounds under conditions permitting binding between a known compound previously shown to be able to displace the polypeptide capable of binding a $p75^{NTR}$ receptor and the $p75^{NTR}$ receptor and the bound $p75^{NTR}$ receptor to form a complex; and (b) detecting the displaced polypeptide capable of binding a $p75^{NTR}$ receptor or the complex formed in step (a), wherein the displacement indicates that the compound is capable of inhibiting specific binding between the polypeptide capable of binding a $p75^{NTR}$ receptor and the $p75^{NTR}$ receptor. In another embodiment of the above described method, wherein the inhibition of specific binding between the polypeptide capable of binding a $p75^{NTR}$ receptor and the $p75^{NTR}$ receptor affects the transcription activity of a reporter gene. In a further embodiment of the above described method, wherein step (b) the displaced polypeptide capable of binding a $p75^{NTR}$ receptor or the complex is detected by comparing the transcription activity of a reporter gene before and after the contacting with the compound in step (a), where a change of the activity indicates that the specific binding between the polypeptide capable of binding a $p75^{NTR}$ receptor and the $p75^{NTR}$ receptor is inhibited and the polypeptide capable of binding a $p75^{NTR}$ receptor is displaced. In an embodiment of the above described method, wherein the $p75^{NTR}$ receptor is bound to a solid support. In a further embodiment of the above described method, wherein the compound is bound to a solid support. In an embodiment of the above described method, wherein the compound comprises an antibody, an inorganic compound, an organic compound, a peptide, a peptidomimetic compound, a polypeptide or a protein. In an embodiment of the above described method, wherein the contacting of step (a) is in vitro. In a further embodiment of the above method, wherein the contacting of step (a) is in vivo. In an embodiment of the above method, wherein the contacting of step (a) is in a yeast cell. In an embodiment of the above method, wherein the contacting or step (a) is in a mammalian cell. In an embodiment of the above method, wherein the polypeptide capable of binding a $p75^{NTR}$ receptor is a cell surface receptor. In an embodiment of the above method, wherein the cell-surface receptor is the p75 receptor.

As used herein, the "transcription activity of a reporter gene" means that the expression level of the reporter gene will be altered from the level observed when the signal-transducing protein and the cytoplasmic protein are bound. One can also identify the compound by detecting other biological functions dependent on the binding between the signal-transducing protein and the cytoplasmic protein. Examples of reporter genes are numerous and well-known in the art, including, but not limited to, histidine resistant genes, ampicillin resistant genes, β-galactosidase gene.

Further the cytoplasmic protein may be bound to a solid support. Also the compound may be bound to a solid support and comprises an antibody, an inorganic compound, an organic compound, a peptide, a peptidomimetic compound, a polypeptide or a protein.

An example of the method is provided infra. One can identify a compound capable of inhibiting specific binding between the signal-transducing protein and the cytoplasmic protein using direct methods of detection such as immunoprecipitation of the cytoplasmic protein and the compound bound to a detectable marker. Further, one could use indirect methods of detection that would detect the increase or decrease in levels of gene expression. As discussed infra, one could construct synthetic peptides fused to a LexA DNA binding domain. These constructs would be transformed into the L40-strain with an appropriate cell line having an appropriate reporter gene. One could then detect whether inhibition had occurred by detecting the levels of expression of the reporter gene. In order to detect the expression levels of the reporter gene, one skilled in the art could employ a variety of well-known methods, e.g. two-hybrid systems in yeast, mammals or other cells.

Further, the contacting of step (a) may be in vitro, in vivo, and specifically in an appropriate cell, e.g. yeast cell or mammalian cell. Examples of mammalian cells include, but not limited to, the mouse fibroblast cell NIH 3T3, CHO cells, HeLa cells, Ltk⁻ cells, Cos cells, etc.

Other suitable cells include, but are not limited to, prokaryotic or eukaryotic cells, e.g. bacterial cells (including gram positive cells), fungal cells, insect cells, and other animals cells.

This invention provides a method of identifying a compound, which is an apoptosis inhibitor, said compound is capable of inhibiting specific binding between human HGR74 protein and $p75^{NTR}$ receptor, so as to prevent apoptosis which comprises: (a) contacting the human HGR74 protein with a plurality of compounds under conditions permitting binding between a known compound previously shown to be able to displace the human HGR74 protein and the $p75^{NTR}$ receptor and the bound $p75^{NTR}$ receptor to form a complex; and (b) detecting the displaced human HGR74 protein or the complex formed in step (a), wherein the displacement indicates that the compound is capable of inhibiting specific binding between the human HGR74 protein and the $p75^{NTR}$ receptor. In an embodiment of the above described method, wherein the inhibition of specific binding between the human HGR74 protein and the $p75^{NTR}$ receptor affects the transcription activity of a reporter gene. In a further embodiment of the above described method, wherein step (b) the displaced human HGR74 protein or the complex is detected by comparing the transcription activity of a reporter gene before and after the contacting with the compound in step (a), where a change of the activity indicates that the specific binding between the human HGR74 protein and the $p75^{NTR}$ receptor is inhibited and the human HGR74 protein is displaced. In an embodiment of the above described method, wherein the $p75^{NTR}$ receptor is bound to a solid support. In a further embodiment of the above described method, wherein the compound is bound to a solid support. In an embodiment of the above described method, wherein the compound comprises an antibody, an inorganic compound, an organic compound, a peptide, a peptidomimetic compound, a polypeptide or a protein. In an embodiment of the above described method, wherein the contacting of step (a) is in vitro. In a further embodiment of the above method, wherein the contacting of step (a) is in vivo. In an embodiment of the above method, wherein the contacting of step (a) is in a yeast cell. In an embodiment of the above method, wherein the contacting or step (a) is in a mammalian cell. In an embodiment of the above method, wherein the human HGR74 protein is a cell surface receptor. In an embodiment of the above method, wherein the cell-surface receptor is the p75 receptor.

As used herein, the "transcription activity of a reporter gene" means that the expression level of the reporter gene will be altered from the level observed when the signal-transducing protein and the cytoplasmic protein are bound. One can also identify the compound by detecting other biological functions dependent on the binding between the signal-transducing protein and the cytoplasmic protein. Examples of reporter genes are numerous and well-known in the art, including, but not limited to, histidine resistant genes, ampicillin resistant genes, β-galactosidase gene.

Further the cytoplasmic protein may be bound to a solid support. Also the compound may be bound to a solid support and comprises an antibody, an inorganic compound, an organic compound, a peptide, a peptidomimetic compound, a polypeptide or a protein.

An example of the method is provided infra. One can identify a compound capable of inhibiting specific binding between the signal-transducing protein and the cytoplasmic protein using direct methods of detection such as immunoprecipitation of the cytoplasmic protein and the compound bound to a detectable marker. Further, one could use indirect methods of detection that would detect the increase or decrease in levels of gene expression. As discussed infra, one could construct synthetic peptides fused to a LexA DNA binding domain. These constructs would be transformed into the L40-strain with an appropriate cell line having an appropriate reporter gene. One could then detect whether inhibition had occurred by detecting the levels of expression of the reporter gene. In order to detect the expression levels of the reporter gene, one skilled in the art could employ a variety of well-known methods, e.g. two-hybrid systems in yeast, mammals or other cells.

Further, the contacting of step (a) may be in vitro, in vivo, and specifically in an appropriate cell, e.g. yeast cell or mammalian cell. Examples of mammalian cells include, but not limited to, the mouse fibroblast cell NIH 3T3, CHO cells, HeLa cells, Ltk⁻ cells, Cos cells, etc.

Other suitable cells include, but are not limited to, prokaryotic or eukaryotic cells, e.g. bacterial cells (including gram positive cells), fungal cells, insect cells, and other animals cells.

In order to facilitate an understanding of the material which follows, certain frequently occurring methods and/or terms are best described in Sambrook, et al., 1989.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Results and Discussions

The p75$^{NTR}$ is the first-isolated neurotrophin receptor and the member of TNFR (tumor necrosis factor receptor) family (7, 8). However, its functional role and signaling pathway has remained largely unclear (9). The existence of p75$^{NTR}$ICD binding proteins have been implicated since p75$^{NTR}$ICD does not have a typical biochemical motif except a C-terminal region well conserved to a type 2 death domain (10). Recently, it has been reported that TRAF6 is involved in p75$^{NTR}$-mediated signal transduction(11). To further identify the p75$^{NTR}$ICD binding proteins, we screened the mouse cDNA libraries by yeast two-hybrid system using a rat p75$^{NTR}$ICD as a target and one of positive clones was identified as a p75$^{NTR}$-associated cell death executor, NADE.

Mouse NADE consists of 124 amino acids and its molecular weight is calculated to 14,532 dalton. NADE is a hydrophilic and acidic protein, and the estimated pI value is 5.97. A BLAST search revealed that mouse NADE has a significant homology to a known human protein HGR74(4) (FIG. 1a), and does not have a significant motif except the leucine rich nuclear export signal (NES) (5) (FIG. 1b) and ubiquitination sequences (6) (FIG. 1c). HGR74 was previously reported as an abundant mRNA expressed in human ovarian granulosa cells, however, its functional role is still unknown. The homology of these two proteins except the asparagine rich stretch (a. a. 36–48) of mouse NADE is 92.8%, therefore we conclude that HGR74 is a human homolog of mouse NADE.

Figure 1D:
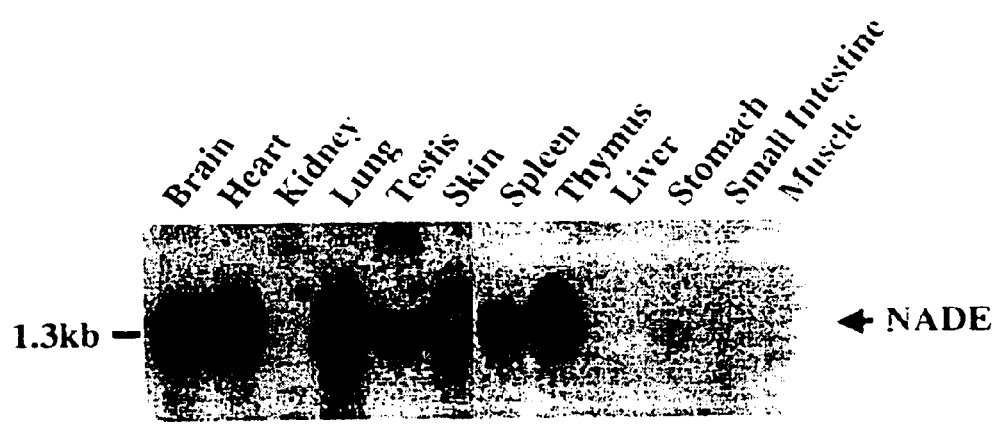
Figure 1E:
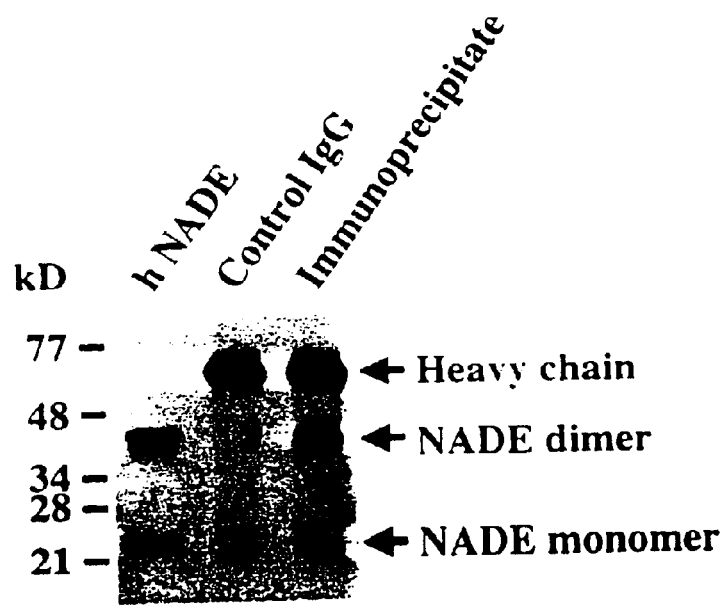
Figure 1F:
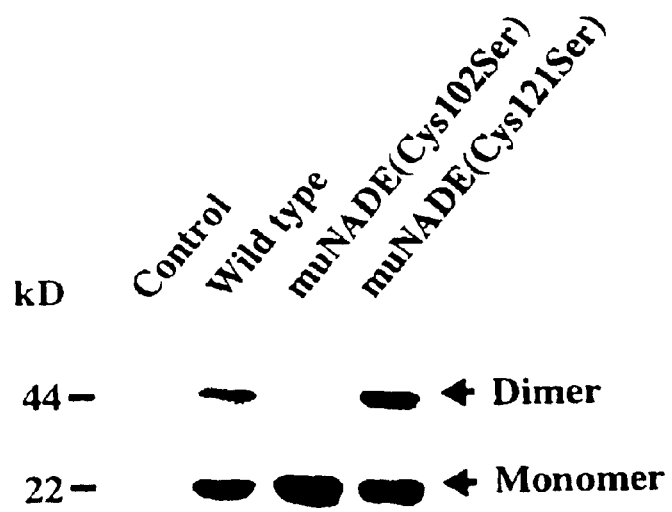

Northern blot analysis is revealed that NADE mRNA (1.3 kbp) is found highest in several tissues including brain, heart, and lung (FIG. 1d). We could also detect a low level of mRNA expression in stomach, small intestine, and muscle by a long exposure (data not shown). But there was no expression in liver. The additional large band (3.0 kbp) was also observed in testis, suggesting the existence of the alternative splicing form. The endogenous NADE protein was also confirmed in human neuroblastoma cell line, SK-N-MC by immunoprecipitation using the anti-NADE antibody (FIG. 1e). Interestingly, in SK-N-MC, PC12 and PCNA cells, NADE protein can be detected only in the presence of the ubiquitin inhibitor such as ALLN, suggesting that NADE is modified by ubiquitin conjugating system leading to subsequent degradation by the proteasome. The molecular size of NADE is estimated to 22 kDa by the SDS-PAGE, and this size seems to be slightly larger than the molecular weight predicted from nucleotide sequence. But the gap of molecular size might be caused by its low pI value or post-translational modification in a potential prenylation site (FIG. 1a). The overexpressed NADE protein in 293T cells showed the two bands, 22 kDa ad 44 kDa in SDS-PAGE under the reduced condition at 100 mM dithiothreitol (FIG. 1f). To clarify this question, two NADE mutants were constructed and expressed in 293T cells. Since NADE has two cysteine residues at sequence positions 102 and 121, we replaced the each cysteine with the serine residue. Western blot analysis revealed that the molecular weight of muNADE (Cys121Ser) is identical to a wild type, on the other hand, muNADE (Cys102Ser) showed the only smaller band of 22 kDa (FIG. 1g). These results strongly suggested that NADE can heterodimerize by the disulfide bound at the Cys102, and resulted in the 44 kDa band.

In vitro-translated mouse NADE protein and E. coli-expressed GST-p75$^{NTR}$ICD fusion protein were used for in vitro GST pull down assay. In this assay, the NADE protein showed the strong binding activity to GST-P p75$^{NTR}$ICD (FIG. 2a). To investigate the in vivo binding activity, the Myc-tagged NADE and p75$^{NTR}$ were co-expressed in 293T cells and subjected to the co-immunoprecipitation experiment. The results clearly showed that NADE could bind to a full length of p75$^{NTR}$ in vivo very strongly (FIG. 2b) and the recruitment of NADE protein to p75$^{NTR}$ICD was detected in a dose dependent of NGF (FIG. 2c), suggesting that NADE protein is a putative signal transducing protein interacting with p75$^{NTR}$ICD. Furthermore, our mapping studies revealed that NADE protein interacts with the cell death domain (amino acid residues 338–393) which is identical among mouse, rat and human (data not shown). Since TRAF6 binds a conserved juxtamembrane region (11), it is unlikely that NADE protein inhibits TRAF6 binding to p75$^{NTR}$ It has been speculated that the polymerization of p75$^{NTR}$ is important for its signal transduction similar to the another members of TNFR family. For example, TNFRI (12), CD40 (13), and Fas (14) are formed the trimer through the binding of each trimer ligands to extracellular domain. However, there was no previous report for p75$^{NTR}$ in same manner (15). It may be possible that the dimer formation of p75$^{NTR}$ occurs through the binding of NADE dimer to its intracellular domain.

Figure 3:
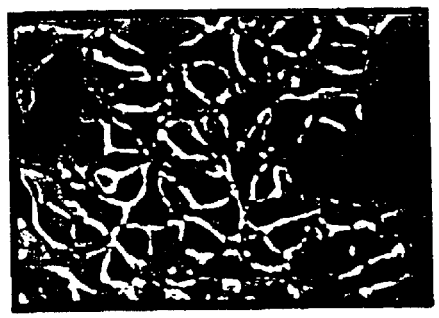
Figure 3:
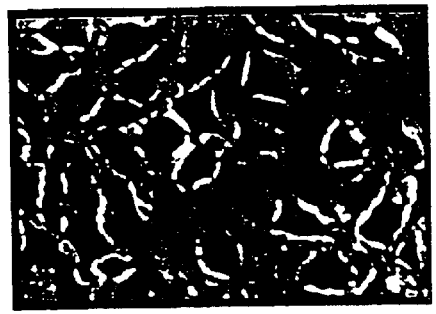
Figure 3:
Figure 3:
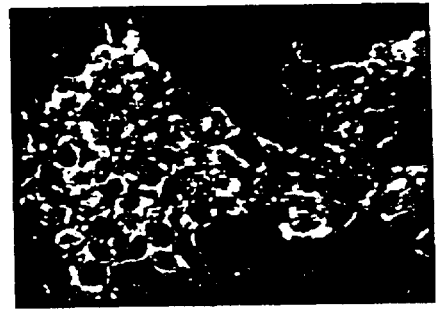
Figure 3C:
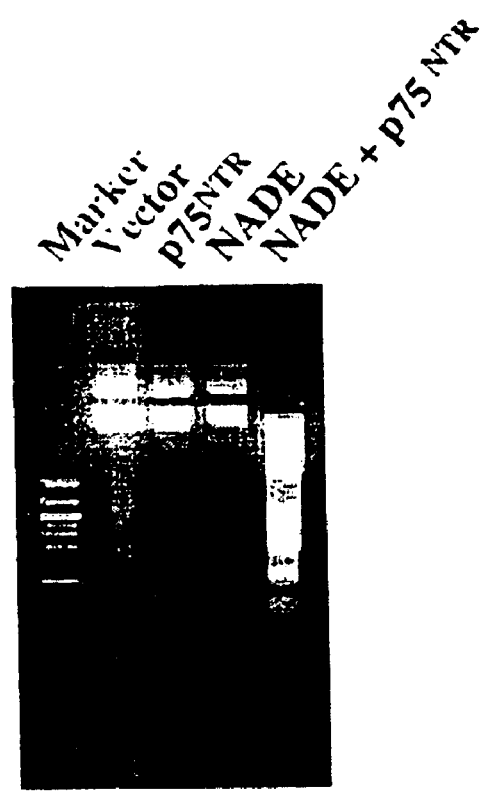
Figure 3D:
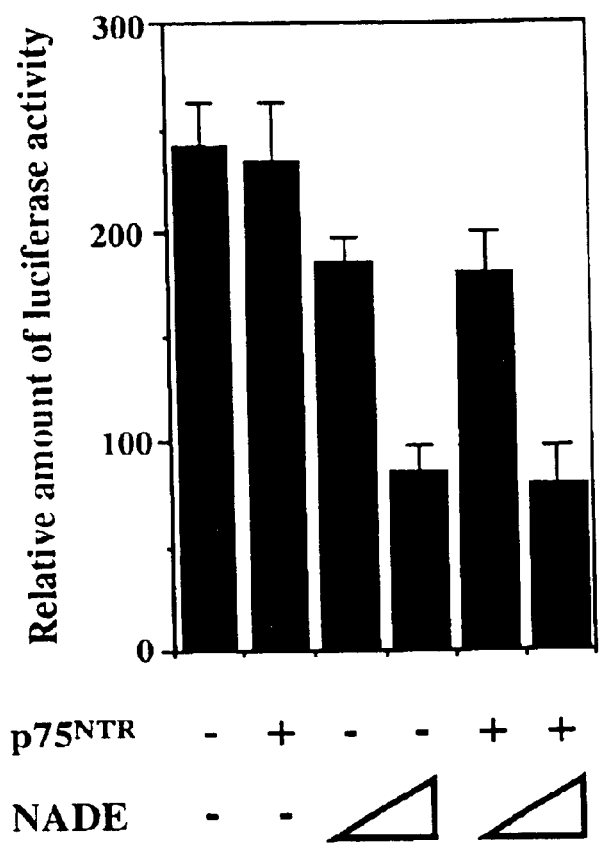

To investigate the functional role of NADE protein, NADE and p75$^{NTR}$ were co-transfected in 293T cells. The results showed that the co-transfected 293T cells were detached from the dish and aggregated 48 hours later (FIG. 3a). However, 293T cells transfected with the control plasmid DNAs showed no significant differences (FIG. 3a), implicating that this morphological change is caused by apoptosis. We further examined the TUNEL assay (TdT-mediated dUTP-biotin nick end labeling assay) (16) as well as the DNA fragmentation test on these cells. On the TUNEL assay, the significant increase of dying cell was detected only in co-transfected cells (FIG. 3b) and the value of the positive cell percentage (38%) was consistent with the transfection efficiency by the calcium-phosphate method. Furthermore, the DNA fragmentation was detected in only the co-transfected 293T cells (FIG. 3c). From these results, we conclude that the co-expression of NADE and p75$^{NTR}$ induced apoptosis in 293T cells.

Although NADE protein is recruited to the cytoplasmic region of p75$^{NTR}$ in a ligand-dependent manner, NGF-dependent cell death was not clearly detected in the co-transfected 293T cells in the presence of NGF (100 ng/ml) (data not shown), suggesting that NADE protein may function in the p75$^{NTR}$-mediated cell death machinery to transduce the downstream signal to apoptosis independent on NGF.

To further investigate the physiological function of NADE protein, we checked the transcription factor kappa B (NF-kB), Caspase-2, and Caspase-3 activities in 293T cells co-transfected with NADE and p75$^{NTR}$ NF-kB is activated by external stimuli, and translocated to the nucleus where it binds to DNA and regulates gene transcription (17). In rat Schwann cells, the binding of NGF to p75$^{NTR}$ induces the activation of NF-kB with independent manner of TrkA (18) leading to the cell survival and TRAF6 may be a component of NGF-mediated NF-kB activation (11). In contrast, expression of NADE protein significantly suppressed the NF-kB activity in a dose dependent manner, but this effect was not markedly co-operative with p75$^{NTR}$ expression (FIG. 3d) as well as NGF-dependent manner (data not shown), implicating that p75$^{NTR}$/NADE-induced apoptosis may not be due to only the suppression of NF-kB activity but also the regulation of unknown signal molecules since NF-kB suppression by NADE protein alone could not induce apoptosis. It has been reported that suppression of NF-kB activity increases cell death in PC12 cells expressing p75$^{NTR}$ (19, 20). NADE protein may play a key role in the downregulation of NF-kB activity and ultimately lead to apoptosis in neuronal cells expressing p75$^{NTR}$.

Figure 3E:
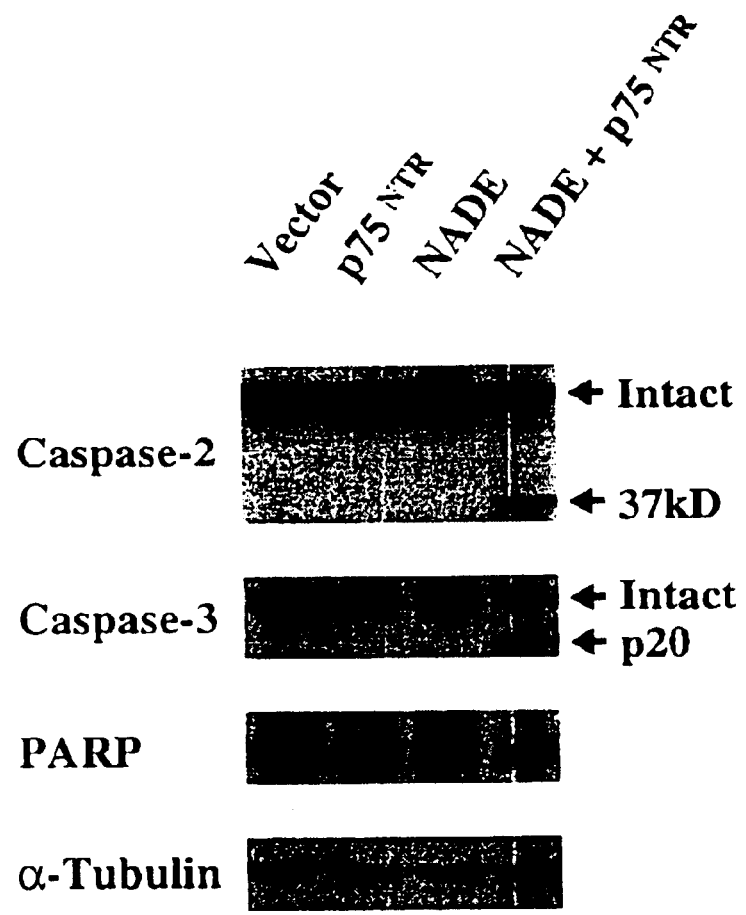

In many cases of apoptosis, the elevation of Caspase-3 activity was observed (21, 22, 23, 24). This protease normally exists in cytosol of cells as 32 kDa precursor that is proteolytically activated into a 20 kDa and a 10 kDa hetrodimer when cells are signaled to undergo apoptosis in response to serum withdrawal, activation of Fas, treatment with ionization, and a variety of pharmacological agents (25). Western blot analysis revealed that Caspase-2 and Caspase-3 were significantly processed only in 293T cells co-transfected with NADE and p75$^{NTR}$ (FIG. 3e). Moreover, PARP (poly (ADP-ribose) polymerase) which is a substrate for both Caspase-2 and Caspase-3 were partially cleaved, indicating that these Caspases are involved in apoptosis mediated by p75$^{NTR}$/NADE signal transduction To investigate whether NES sequences (5) contained in NADE (FIG. 4a) have the capability to export a protein from the nucleus to the cytosol, we performed the transient expression in 293T cells using a series of NADE mutants. The results indicated that NADE proteins with NES sequences localize in the cytoplasmic region (FIG. 4, lower panels of b, upper panels of c and d), but NADE proteins with NES mutations express in the nucleus (FIG. 4, lower panel of c and d). These data support the hypothesis that NADE protein can be exported from the nucleus to the cytosol and may be post-translationally modified as a prenylated protein to promote and regulate p75$^{NTR}$/NADE physiological interaction.

The signal cascade mediated by p75$^{NTR}$ has been enigmatic for a long time. But the recent growing evidences indicate that, not like other members of TNFR family, p75$^{NTR}$ can bifunctionally mediate signals to induce and inhibit apoptosis (26, 27). Our results strongly supported that NADE is a putative signal transducer for p75$^{NTR}$-mediated apoptosis. Although NADE can mediate apoptosis cooperative with p75$^{NTR}$, it is possible that NADE may be a signal adaptor molecule to interact with another effector molecules in p75$^{NTR}$-mediated signal transduction. More importantly, since NADE has nuclear export signal (NES) as well as ubiquitination sequence, NADE may be tightly controlled by the ubiquitin/proteasome to shuttle another molecule from the nucleus to the cytoplasm, implicating that NADE is a very important protein for turnover of regulator gene such as the cell cycle-related proteins. Further investigation under physiological condition will give us more insight to better understand the mechanisms by which NADE can induce apoptosis together with p75$^{NTR}$ expression.

Methods
Isolation of p75$^{NTR}$-associated Cell Death Executor (NADE) by Yeast Two-hybrid System.

In order to isolate cDNA encoding p75$^{NTR}$-associated proteins, we used yeast two-hybrid system, originally developed by Fields and Song (28). We used the cytosolic domain of rat p75$^{NTR}$ cDNA corresponding to amino acids 338–396 (representing the cytosolic domain of the protein from the transmenbrane domain to the C-terminus of the protein) as a target. This portion of p75$^{NTR}$ cDNA was PCR-engineered into the yeast expression plasmid pBTM116 in-frame with sequences encoding the LexA DNA-binding domain (29). This plasmid was then introduced into L40 cells [a, his3, trp1, leu2, ade2, lys2: (lexAop)$^4$-HIS3, URA3: (lexAop)$^8$-lacZ] which contain histidine synthetase (HIS3) and b-galactosidase (lacZ) reporter genes under the control of lexA operators (29). After confirming the expression of LexA-p75$^{NTR}$ (338-396) protein by immunoblotting using an antiserum specific for LexA, a mouse embryo pVP16 cDNA libraries were then introduced into these LexA/ p75$^{NTR}$-expressing cells by a high efficiency LiOAc transformation method (30, 31, 32). From a screen of 5×10$^7$ transformants, an initial set of 672 His$^+$ colonies were identified. These 672 clones were then tested by a β-galactosidase colorimetric assay (33), utilizing the lacZ reporter gene under the control of 8 lexA operators, thus narrowing down the pool of candidate clones to 181, These 181 candidates were then "cured" of their LexA/p75$^{NTR}$-encoding plasmids by growth in tryptophan containing media, and mated with a panel of Mata-type yeast strain NA87-11A [a, leu2, his3, trp1, pho3, pho5] into which we had introduced various control plasmids that produce LexA fusion proteins, including LexA/p75$^{NTR}$, LexA/Ras, Lex/ CD40, LexA/Fas, and LexA/lamin. Among the 181 candidate clones, 1 clone specifically reacted with the LexA/ p75$^{NTR}$ protein was chosen for further analysis. This mouse cDNA clone No. 59 has insert sizes of 450 bp. Because of its ability to induce cell death with expression of p75$^{NTR}$, we have named this protein, NADE (p75$^{NTR}$-associated cell death executor).

DNA Construction.

A full length mouse NADE cDNA was constructed on pBluescript II vector by the ligation of the partial NADE cDNA (7-524) and 5'-RACE product. PCR cloning techniques were used to replace the stop codon and add the 5' XhoI site and 3' BaniHI site of a full length NADE cDNA. pcDNA3.1(−)MyC-HisA/NADE was constructed by insertion of a full length NADE cDNA to XhoI-BamHI site of pcDNA3.1(−)Myc-HisA (Invitrogen). Human NADE cDNA was amplified using a Jurkat T cell cDNA library and cloned to pcDNA3.1(−)Myc-HisA pcDNA3/rat p75$^{NTR}$ was constructed by insertion of a full length rat p75$^{NTR}$ cDNA to EcoRI site of pcDNA3(Invitrogen). pGEX4T-1/rat p75$^{NTR}$ICD was constructed by insertion of amplified rat p75$^{NTR}$ICD(a. a. 338–396) to pGEX4T-l(Pharmacia). Mutant NADE expression plasmids, pcDNA3.1(−)Myc-HisA/muNADE (Cys102Ser) and pcDNA3 .1 (−)Myc-HisA/muNADE(Cys121Ser), were constructed by PCR-based site-direct mutagenesis methods (29). pELAN-Lu for luciferase reporter assay was constructed by insertion of NF-κB binding site of E-selectin promoter region (−730 -52) to pGL3-Basic SacI-BglII site. Expression plasmids of GFP-fused NADE proteins were made following: The cDNA of GFP was cloned into NheI-XhoI-cut pcDNA3.1-mouse NADE as a PCR product amplified with the primers 5"-CTAGCTAGCATCATGGTGAGCAAGGG-CGAG- 3"(SEQ. ID NO:3) and 5"-CCGCTCGAGTCTTG-TACAGCTCGTCCAT-3"(SEQ. ID NO:4) using pEGFP-N2 (Clontech) as a template. The deletion mutants delta 101-124-GFP and delta 91-124-GFP were constructed by inserting an XhoI-BamHI-cut PCR fragment generated with Expand high fidelity Taq polimerase (Boehringer Mannheim) into XhoI-BamHI-cut pcDNA3.1-GFP using the primers 5"-ATCCTCGAGCGATCATGGCCAATGTCCAC-3" (sense) (SEQ. ID NO:5)

5"-ATCGGATCCTCTCAGCTGTAGCTCCCT-3" (antisense) (SEQ. ID NO:6)

and

5"-ATCGGATCCGATCTCTCTCATCTCCTC-3" (antisense) (SEQ. ID NO:7).

The mutagenic primers (5'-AAAGCTTAGGGAGGCACAGCTGAGAAA-3" (SEQ. ID NO:8),

5"-TTTCTCAGCTGTGCCTCCCTAAGCTTT-3" (SEQ. ID NO:9),

5"-ATCCGGAGAAAGGCTAGGGAGGCACA-3" (SEQ. ID NO:10), and

5"-TGTGCCTCCCTAGCCTTTCTCCGGAT-3") (SEQ. ID NO:11)

were used to obtain L97A-GFP and L94, 97A-GFP in which Leu94 and Leu97 are replaced with Ala. In all constructs, mutations were verified by sequencing.

Northern blot analysis. 400 ng of NADE cDNA fragments (nt. 5–510) were labeled by 50 $\mu$Cl of [a-$^{32}$P]dCTP and used as a probe. Each 10 $\mu$g of total mRNA extracted from mouse various tissues were transferred on membranes and they were hybridized with a NADE probe for 2 hours at 68° C. using a express hybrid buffer (Clontech) and washed with 2×SSC, 0.05% SDS for 5 times, and 0.1×SSC, 0.1% SDS for 1 time.

Antibodies. The polyclonal anti-NADE antibody was prepared by immunization of GST-mouse NADE fusion protein into the rabbit. The NADE specific antibody was affinity purified by antigen coupled Sepharose 4B. The polyclonal anti-rat p75$^{NTR}$ was kindly gifted from Dr. M. V. Chao. The monoclonal anti-Myc antibody (9E10) was purchased from BIOMOL. The polyclonal anti-Caspase-3 antibody (H-277) was purchased from Santa Cruz Biotechnology. The polyclonal Caspase-2 antibody was kindly gifted from Dr. Lloyd A. Greene HRP conjugated anti-rabbit IgG was purchased from Bio-Rad.

Immunoprecipitation and immunoblotting. In FIG. 1e, 150 $\mu$g/ml of ALLN (N-Acetyl-Leu-Leu-Norleucinal) treated SK-N-MC cells (1×10$^7$) were lysed in 0.5 ml of RIPA buffer. The supernatant of centrifuge (100,000×g) was mixed with 1 $\mu$g of polyclonal anti-NADE antibody coupled Sepharose 4B, and incubated for 4 hours at 4° C. After washing, the gels were boiled by 30 $\mu$l of SDS-PAGE sampling buffer and subjected to 12.5% of SDS-PAGE. Immunoblotting was performed by polyclonal anti-NADE antibody (2 $\mu$g/ml). In FIG. 1f, 10 $\mu$g of cell lysate extracted from each transfected 293T cells were used for the detection of NADE by immunoblotting.

Transfection and protein expression in 293T cell. In FIG. 1f, 293T cells (2×10$^6$) were transfected by 10 $\mu$g of pcDNA3.1(-)Myc-HisA/NADE, pcDNA3.1(-)Myc-HisA/muNADE (Cys102Ser), or pcDNA3.1(-)Myc-HisA/muNADE(Cys121Ser) by calcium-phosphate method. In FIGS. 2b, 3a, b, c, e, 293T cells (2×10$^6$) were transfected by 20 $\mu$g of pcDNA3.1(-) Myc-HisA, $\mu$10 g of pcDNA3/rat p75$^{NTR}$ and 10 $\mu$g of pcDNA3.1(-) Myc-HisA, 10 $\mu$g of pcDNA3.1(-)Myc-HisA NADE and 10 g of pcDNA3.1(-) Myc-HisA, or 10 $\mu$g of pcDNA3.1(-)Myc-HisA/NADE and 10 $\mu$g of pcDNA3/rat p75$^{NTR}$. In FIG. 2c, 293T cells (2×10$^6$) were transfected by 10 $\mu$g of pcDNA3.1(-)Myc-HisA/NADE and 10 $\mu$g of pcDNA3/rat p75$^{NTR}$ in serum minus DMEM medium.

In vitro binding assay. 5 $\mu$l of L-[$^{35}$S] methionine labeled, and in vitro-translated NADE protein was mixed with 5 $\mu$l of GST-rat p75$^{NTR}$ICD fusion protein or GST-coupled GSH-Sepharose 4B (Pharmacia) in 100 $\mu$l of NETN buffer (20 mM Tris-HCl pH 8.0, 100 mM NaCl, 1 mM EDTA, 0.2% W NP-40) for 18 hours at 4° C. After washing, gels were boiled by 30 $\mu$l of SDS-PAGE sampling buffer and subjected to 13.5% SDS-PAGE. The fluolography was performed for 16 hours at −70° C.

In vivo binding assay. In FIG. 2b, transfected 293T cells by were lysed in 1 ml of NETN buffer and centrifuged (100,000 $\mu$g). The supernatants were immunoprecipitated by 2 $\mu$g of anti-Myc antibody coupled Protein G Sepharose 4B (Pharmacia) for 2 hours at 4° C. Following the 5 times washing, gels were subjected to 7.5% SDS-PAGE, and Western blot analysis by rabbit polyclonal anti-p75$^{NTR}$ antibody.

Interaction of NADE with p75$^{NTR}$ dependent on NGF ligation. After co-transfection, cells were incubated in DMEM medium containing various NGF. After 12 hours later, the interaction activity between NADE and p75$^{NTR}$ were checked by in vivo binding assay.

TUNEL assay. MEBSTAIN Apoptosis kit direct (MIC) was used for TUNEL assay and the assay was done according to the company instruction. The stained cells were analyzed by FACSCalibur flow cytometer (Becton Dickinson).

DNA fragmentation assay. Transfected 293T cells were lysed in 350 $\mu$l of 10 mM EDTA and 0.5% SDS for 10 minutes at room temperature. After adding 100 $\mu$l of 5 M NaCl, the aliquot was incubated for 18 hours at 4° C. and centrifuged (12,000×g). The supernatants were treated by 1 mg/ml of RNase A and 50 ng/ml of Proteinase K for 2 hours at 42° C. After the phenolchloroform extraction, the DNAs were precipitated by 70% ethanol, and dissolved in 30 $\mu$l of H$_2$O. 5 $\mu$l of samples were subjected to the 1.5% agarose gel electrophoresis.

Measurement of NF-B activity. Dual-Luciferase Reporter Assay System (Promega) was used for measurement of NF-κB activity. 293T cells (4×10$^5$) were transfected with 1.5 $\mu$g of pELAM-luc reporter plasmid, 0.1 $\mu$g of pRL-TK, 0.7 $\mu$g of pcDNA3 rat p75$^{NTR}$, 0.3 $\mu$g or 2.8 $\mu$g of pcDNA3.1(-) Myc-HisA/NADE and enough pcDNA3.1(-) Myc-His a control plasmid to give 5.1 $\mu$g of total DNA. Luciferase activities were determined 24 hours after transfection and normalized on the basis of pRL-TK expression levels. The luciferase activities were measured by Turner Designs Luminometer Model TD20/20 (Promega).

Confocal Laser Microscopy

Transient transfections were carried out using the calcium phosphate precipitation method. 293T cells (3×10$^5$) on a cover glass were transiently transfected with 3.0 ug of DNA. After 12–24 hours, cells were fixed with 4% paraformaldehyde and stained with TO-PRO-3 Iodide (Molecular Probes, Inc.) to visualize the nucleus. The subcellular distribution of GFP fusion proteins was examined using confocal laser microscopy (Carl Zeiss LSM510).

REFERENCES

1. Rabizadeh, S., Oh, J., Zhong, L. T., Yang, J., Bitler, C. M., Butcher, L. L. & Bredesen, D. E.,. Induction of apoptosis by the low-affinity NGF receptor. *Science* 261, 345–348 (1993).
2. Frade, J. M., Rodriguez-Tebar, A. & Barde, Y. A.,. Induction of cell death by endogenous nerve growth factor through its p75 receptor. *Nature* 383 166–168 (1996).
3. Barrett, G. L. & Bartlett, P. F. The p75 nerve growth factor receptor mediates survival or death depending on the stage of sensory neuron development. *Proc. Natl. Acad. Sci. USA* 91, 6501–6505 (1994).
4. Rapp, G., Freudenstein, J., Klaudiny, J., Mucha, J., Wempe, F., Zimmer, M. & Scheit, K. H. Characterization of three abundant mRNAs from human ovarian granulosa cells. *DNA Cell. Biol.* 9, 479–485 (1990).
5. Nakielny, S. & Dreyfuss, G. Nuclear export of proteins and RNAs. *Curr Opin Cell Biol.* 9, 420–429 (1997).
6. Ciechanover, A. The ubiquitin-proteasome pathway: on protein death and cell life. *EMBO J.* 17, 7151–7160 (1998).
7. Johnson, D., Lanahan, A., Buck, C. R., Sehgal, A., Morgan, C., Mercer, E., Bothwell, M. & Chao, M. V. Expression and structure of the human NGF receptor. *Cell* 47, 545–554 (1986).
8. Chao, M. V. & Hempstead, B. L. p75 and Trk: a two-receptor system. *Trends Neurosci.* 18, 321–326 (1995).
9. Kaplan, D. R. & Miller, F. D. Signal transduction by the neurotrophin receptors. *Curr. Opin. Cell Biol.* 9, 213–221 (1997).
10. Feinstein, E., Kimchi, A., Wallach, D., Boldin, M. & Varfolomeev, E. The death domain: a module shared by proteins with diverse cellular functions. *Trends Biochem. Sci.* 20, 342–344 (1995).
11. Khursigara, G., Orlinick, J. R. & Chao, M. V. Association of tile p75 neurotrophin receptor with TRAF6. *J Biol Chem.* 274, 2597–2600 (1999).
12. Smith, R. A. & Baglioni, C. The active form of tumor necrosis factor is a trimer. *J. Biol. Chem.* 262, 6951–6954 (1987).
13. Pietravalle, F., Lecoanet-Henchoz, S., Blasey, H., Aubry, J. P., Elson, G., Edgerton, M. D., Bonnefoy, J. Y. & Gauchat, J. F. Human native soluble CD40L is a biologically active trimer, processed inside microsomes. *J. Biol. Chem.* 271, 5965–5967 (1996).
14. Tanaka, M., Suda, T., Takahashi, T. & Nagata, S. Expression of the functional soluble form of human fas ligand in activated lymphocytes. *EMBO J.* 14, 1129–1135 (1995).
15. Liepinsh, E., Ilag, L. L., Otting, G. & Ibanez, C. F. NMR structure of the death domain of the p75 neurotrophin receptor. *EMBO J.* 16, 4999–5005 (1997).
16. Gavrieli, Y., Sherman, Y. & Ben-Sasson, S. A. Identification of programmed cell death in situ via specific labeling of nuclear DNA fragmentation. *J. Cell. Biol.* 119, 493–501 (1992).
17. Baeuerle, P. A. & Henkel, T. Function and activation of NF-kappa B in the immune system. *Annu Rev Immunol* 12, 142–179 (1994).
18. Carter, B. D., Kaltschmidt, C., Kaltschmidt, B., Offenhauser, N., Bohm-Matthaei, R., Baeuerle, P. A. & Barde, Y. A. Selective activation of NF-kappa B by nerve growth factor through the neurotrophin receptor p75. *Science* 272, 542–545 (1996).
19. Taglialatela, G., Robinson, R. & Perez-Polo, J. R. Inhibition of nuclear factor kappa B (NFkappaB) actively induces nerve growth factor-resistant apoptosis in PC12 cells. *J. Neurosci Res.* 47, 155–162 (1997).
20. Lezoualc'h, F., Sagara, Y., Holsboer, F. & Behl, C. High constitutive NF-kappa B actively mediates resistance to oxidative stress in neuronal cells. *J. Neurosci.* 18, 3224–3232 (1998).
21. Stefanis, L., Troy, C. M., Qi, H., Shelanski, M. L. & Greene, L. A. Caspase-2 (Nedd-2) processing and death of trophic factor-deprived PC12 cells and sympathetic neurons occur independently of caspase-3 (CPP32)-like activity. *J Neurosci.* 18, 9204–9215 (1998).
22. Fernandes-Alnemri, T., Litwack, G. & Alnemri, E. S. CPP32, a novel human apoptotic protein with homology to *Caenorhabditis elegans* cell death protein Ced-3 and mammalian interleukin-1 beta-converting enzyme. *J. Biol. Chem.* 269, 30761–30764 (1994).
23. Tewari, M., Quan, L. T., O'Rourke, K., Desnoyers, S., Zeng, Z., Beidler, D. R., Poirier, G. G., Salvesen, G. S. & Dixit, V. M. Yama/CPP32 beta, a mammalian homolog of CED-3, is a CrmA-inhibitable protease that cleaves the death substrate poly(ADP-ribose) polymerase. *Cell* 81, 801–809 (1995).
24. Schlegel, J., Peters, I., Orrenius, S., Miller, D. K., Thornberry, N. A., Yamin, T. T. & Nicholson, D. W. CPP32/apopain is a key interleukin 1 beta converting enzyme-like protease involved in Fas-mediated apoptosis. *J. Biol. Chem.* 271, 1841–1844 (1996).
25. Datta, R., Banach, D., Kojima, H., Talanian, R. V., Alnemri, E. S., Wong, W. W. & Kufe, D. W. Activation of the CPP32 protease in apoptosis induced by 1-beta-D-arabinofuranosylcytosine and other DNA-damaging agents. *Blood* 88, 1936–1943 (1996).
26. Casaccia-Bonnefil, P., Carter, B. D., Dobrowsky, R. T. & Chao, M. V. Death of oligodendrocytes mediated by the interaction of nerve growth factor with its receptor p75. *Nature* 383, 716–719 (1996).
27. Bunone, G., Mariotti, A., Compagni, A., Morandi, E. & Della Valle, G. Induction of apoptosis by p75 neurotrophin receptor in human neuroblastoma cells. *Oncogene* 14, 1463–1470 (1997).
28. Fields, S. & Song, O. A novel genetic system to detect protein-protein interactions. *Nature* 340, 245–246 (1989).
29. Vojtek, A. B., Hollenberg, S. M. & Cooper, J. A. Mammalian Ras interacts directly with the serine/threonine kinase Raf. *Cell* 74, 205–214 (1993).
30. Ito, H., Fukuda, Y., Murata, K. & Kimura, A. Transformation of intact yeast cells treated with alkaline cations. *J. Bacteriol.* 153, 163–168 (1983).
31. Gietz, D., Jean, A. S., Woods, R. A. & Schiestl, R. H. Improved method for high efficiency transformation of intact yeast cells. *Null. Acids Res.* 20, 1425 (1992).
32. Schiestl, R. H. & Gist, R. D. High efficiency transformation of intact cells using single stranded nucleic acids as a carrier. *Curr. Gene.* 16, 339–346 (1989).
33. Breeder, L. & Nasmyth, K. Regulation of the yeast HO gene. *Cold Spring Harbor Sump. Quant. Biol.* 50, 643–650 (1985).
34. Weiner, M. P., Felts, K. A., Simcox, T. G. & Braman, J. C. A method for the site-directed mono- and multi-mutagenesis of double-stranded DNA. *Gene* 126, 35–41 (1993).

What is claimed is:

1. A method for determining whether an agent may be an apoptosis inhibitor comprising:
   (a) contacting the agent with a NADE protein and a p75 neurotrophin receptor in vitro under conditions which, in the absence of the agent, permit the formation of a complex between the NADE protein and the receptor;
   (b) determining the amount of complex formed in step (a) between the NADE protein and the receptor; and
   (c) determining whether the amount of complex determined in step (b) is less than the amount of complex formed in the absence of the agent, such lower amount indicating that the agent may be an apoptosis inhibitor.

2. A method for determining whether an agent may be an apoptosis inducer comprising:
   (a) contacting the agent with a NADE protein and a p75 neurotrophin receptor in vitro under conditions which, in the absence of the agent, permit the formation of a complex between the NADE protein and the receptor;
   (b) determining the amount of complex formed in step (a) between the NADE protein and the receptor; and
   (c) determining whether the amount of complex determined in step (b) is greater than the amount of complex formed in the absence of the agent, such greater amount indicating that the agent may be an apoptosis inducer.

3. The method of claim 1 or 2, wherein the NADE protein comprises the amino acid sequence as set forth in SEQ ID NO:13.

4. The method of claim 1 or 2, wherein the contacting of step (a) is not performed in an intact cell.

5. A method for determining whether an agent may be an apoptosis inhibitor comprising:
   (a) contacting the agent in vitro with a cell that expresses a NADE protein and a p75 neurotrophin receptor;
   (b) determining the expression level of the NADE protein in the cell; and
   (c) determining whether the expression level determined in step (b) is lower than the NADE protein expression level determined in the absence of the agent, such lower expression level indicating that the agent may be an apoptosis inhibitor.

6. A method for determining whether an agent may be an apoptosis inducer comprising:
   (a) contacting the agent in vitro with a cell that expresses a NADE protein and a p75 neurotrophin receptor;
   (b) determining the expression level of the NADE protein in the cell; and
   (c) determining whether the expression level determined in step (b) is greater than the NADE protein expression level determined in the absence of the agent, such greater expression level indicating that the agent may be an apoptosis inducer.

7. The method of claim 5 or 6, wherein the NADE protein comprises the amino acid sequence as set forth in SEQ ID NO:13.

8. The method of claim 5 or 6, wherein the cell is a neuron, a cardiac cell, or a lung cell.

* * * * *

SEQUENCE LISTING

<160> NUMBER OF SEQ ID NOS: 45

<210> SEQ ID NO 1
<211> LENGTH: 36
<212> TYPE: DNA
<213> ORGANISM: Mouse

<400> SEQUENCE: 1
aattgtctac gcatccttat gggggagctg tctaac                                   36

<210> SEQ ID NO 2
<211> LENGTH: 12
<212> TYPE: PRT
<213> ORGANISM: Mouse

<400> SEQUENCE: 2

Asn Cys Leu Arg Ile Leu Met Gly Glu Leu Ser Asn
1               5                   10

<210> SEQ ID NO 3
<211> LENGTH: 30
<212> TYPE: DNA
<213> ORGANISM: Artificial Sequence
<220> FEATURE:
<223> OTHER INFORMATION: Mouse Nade DNA

<400> SEQUENCE: 3
ctagctagca tcatggtgag caagggcgag                                          30

<210> SEQ ID NO 4
<211> LENGTH: 28
<212> TYPE: DNA
<213> ORGANISM: Artificial Sequence
<220> FEATURE:
<223> OTHER INFORMATION: Mouse Nade DNA

<400> SEQUENCE: 4
ccgctcgagt cttgtacagc tcgtccat                                            28

<210> SEQ ID NO 5
<211> LENGTH: 29
<212> TYPE: DNA
<213> ORGANISM: Artificial Sequence
<220> FEATURE:
<223> OTHER INFORMATION: Mouse Nade DNA

<400> SEQUENCE: 5
atcctcgagc gatcatggcc aatgtccac                                           29

<210> SEQ ID NO 6
<211> LENGTH: 27
<212> TYPE: DNA
<213> ORGANISM: Artificial Sequence
<220> FEATURE:
<223> OTHER INFORMATION: Mouse Nade DNA

<400> SEQUENCE: 6
atcggatcct ctcagctgta gctccct                                             27

<210> SEQ ID NO 7
<211> LENGTH: 27
<212> TYPE: DNA
<213> ORGANISM: Artificial Sequence
<220> FEATURE:

```
<223> OTHER INFORMATION: Mouse Nade DNA

<400> SEQUENCE: 7
atcggatccg atctctctca tctcctc                                        27

<210> SEQ ID NO 8
<211> LENGTH: 27
<212> TYPE: DNA
<213> ORGANISM: Artificial Sequence
<220> FEATURE:
<223> OTHER INFORMATION: Mouse Nade DNA

<400> SEQUENCE: 8
aaagcttagg gaggcacagc tgagaaa                                        27

<210> SEQ ID NO 9
<211> LENGTH: 27
<212> TYPE: DNA
<213> ORGANISM: Artificial Sequence
<220> FEATURE:
<223> OTHER INFORMATION: Mouse Nade DNA

<400> SEQUENCE: 9
tttctcagct gtgcctccct aagcttt                                        27

<210> SEQ ID NO 10
<211> LENGTH: 26
<212> TYPE: DNA
<213> ORGANISM: Artificial Sequence
<220> FEATURE:
<223> OTHER INFORMATION: Mouse Nade DNA

<400> SEQUENCE: 10
atccggagaa aggctaggga ggcaca                                         26

<210> SEQ ID NO 11
<211> LENGTH: 26
<212> TYPE: DNA
<213> ORGANISM: Artificial Sequence
<220> FEATURE:
<223> OTHER INFORMATION: Mouse Nade DNA

<400> SEQUENCE: 11
tgtgcctccc tagcctttct ccggat                                         26

<210> SEQ ID NO 12
<211> LENGTH: 124
<212> TYPE: PRT
<213> ORGANISM: Mouse

<400> SEQUENCE: 12

Met Ala Asn Val His Gln Glu Asn Glu Glu Met Glu Gln Pro Leu Gln
 1               5                  10                  15

Asn Gly Glu Glu Asp Arg Pro Val Gly Gly Glu Gly His Gln Pro
             20                  25                  30

Ala Gly Asn Asn Asn Asn Asn Asn His Asn His Asn His Asn His His
         35                  40                  45

Arg Arg Gly Gln Ala Arg Arg Leu Ala Pro Asn Phe Arg Trp Ala Ile
     50                  55                  60

Pro Asn Arg Gln Met Asn Asp Gly Leu Gly Gly Asp Gly Asp Asp Met
65                  70                  75                  80

Glu Met Phe Met Glu Glu Met Arg Glu Ile Arg Arg Lys Leu Arg Glu
                85                  90                  95
```

```
Leu Gln Leu Arg Asn Cys Leu Arg Ile Leu Met Gly Glu Leu Ser Asn
            100                 105                 110

His His Asp His His Asp Glu Phe Cys Leu Met Pro
        115                 120

<210> SEQ ID NO 13
<211> LENGTH: 111
<212> TYPE: PRT
<213> ORGANISM: Human

<400> SEQUENCE: 13

Met Ala Asn Ile His Gln Glu Asn Glu Glu Met Glu Gln Pro Met Gln
 1               5                  10                  15

Asn Gly Glu Glu Asp Arg Pro Leu Gly Gly Glu Gly His Gln Pro
            20                  25                  30

Ala Gly Asn Arg Arg Gly Gln Ala Arg Arg Leu Ala Pro Asn Phe Arg
            35                  40                  45

Trp Ala Ile Pro Asn Arg Gln Ile Asn Asp Gly Met Gly Gly Asp Gly
        50                  55                  60

Asp Asp Met Glu Ile Phe Met Glu Glu Met Arg Glu Ile Arg Arg Lys
65                  70                  75                  80

Leu Arg Glu Leu Gln Leu Arg Asn Cys Leu Arg Ile Leu Met Gly Glu
                85                  90                  95

Leu Ser Asn His His Asp His His Asp Glu Phe Cys Leu Met Pro
            100                 105                 110

<210> SEQ ID NO 14
<211> LENGTH: 13
<212> TYPE: PRT
<213> ORGANISM: Mouse

<400> SEQUENCE: 14

Leu Thr Met Lys Glu Val Glu Glu Leu Glu Leu Leu Thr
 1               5                  10

<210> SEQ ID NO 15
<211> LENGTH: 13
<212> TYPE: PRT
<213> ORGANISM: Mouse

<400> SEQUENCE: 15

Ala Leu Gln Lys Lys Leu Glu Glu Leu Glu Leu Asp Glu
 1               5                  10

<210> SEQ ID NO 16
<211> LENGTH: 10
<212> TYPE: PRT
<213> ORGANISM: Mouse

<400> SEQUENCE: 16

Leu Ala Leu Lys Leu Ala Gly Leu Asp Ile
 1               5                  10

<210> SEQ ID NO 17
<211> LENGTH: 9
<212> TYPE: PRT
<213> ORGANISM: Mouse

<400> SEQUENCE: 17

Leu Pro Val Leu Glu Asn Leu Thr Leu
 1               5
```

```
<210> SEQ ID NO 18
<211> LENGTH: 9
<212> TYPE: PRT
<213> ORGANISM: Mouse

<400> SEQUENCE: 18

Leu Pro Pro Leu Glu Arg Leu Thr Leu
1               5

<210> SEQ ID NO 19
<211> LENGTH: 12
<212> TYPE: PRT
<213> ORGANISM: Mouse

<400> SEQUENCE: 19

Lys Val Ala Glu Lys Leu Glu Ala Leu Ser Val Arg
1               5                   10

<210> SEQ ID NO 20
<211> LENGTH: 13
<212> TYPE: PRT
<213> ORGANISM: Mouse

<400> SEQUENCE: 20

Glu Val Asp Gln Leu Arg Leu Glu Arg Leu Gln Ile Asp
1               5                   10

<210> SEQ ID NO 21
<211> LENGTH: 8
<212> TYPE: PRT
<213> ORGANISM: Mouse

<400> SEQUENCE: 21

Leu Pro Leu Gly Lys Leu Thr Leu
1               5

<210> SEQ ID NO 22
<211> LENGTH: 14
<212> TYPE: PRT
<213> ORGANISM: Human

<400> SEQUENCE: 22

Ala Leu Ser Ala Gln Leu Tyr Ser Ser Leu Ser Leu Asp Ser
1               5                   10

<210> SEQ ID NO 23
<211> LENGTH: 13
<212> TYPE: PRT
<213> ORGANISM: Mouse

<400> SEQUENCE: 23

Arg Glu Ile Arg Arg Lys Leu Arg Glu Leu Gln Leu Arg
1               5                   10

<210> SEQ ID NO 24
<211> LENGTH: 13
<212> TYPE: PRT
<213> ORGANISM: Mouse

<400> SEQUENCE: 24

Arg Glu Ile Arg Arg Lys Leu Arg Glu Leu Gln Leu Arg
1               5                   10
```

```
<210> SEQ ID NO 25
<211> LENGTH: 27
<212> TYPE: PRT
<213> ORGANISM: Mouse

<400> SEQUENCE: 25

Arg Glu Ile Arg Arg Lys Leu Arg Glu Leu Gln Leu Arg Asn Cys Leu
 1               5                  10                  15

Arg Ile Leu Met Gly Glu Leu Ser Asn His His
            20                  25

<210> SEQ ID NO 26
<211> LENGTH: 27
<212> TYPE: PRT
<213> ORGANISM: Human

<400> SEQUENCE: 26

Arg Glu Ile Arg Arg Lys Leu Arg Glu Leu Gln Leu Arg Asn Cys Leu
 1               5                  10                  15

Arg Ile Leu Met Gly Glu Leu Ser Asn His His
            20                  25

<210> SEQ ID NO 27
<211> LENGTH: 8
<212> TYPE: PRT
<213> ORGANISM: Mouse

<400> SEQUENCE: 27

Arg Leu Leu Asn Arg Leu Leu Asn
 1               5

<210> SEQ ID NO 28
<211> LENGTH: 700
<212> TYPE: DNA
<213> ORGANISM: Mouse

<400> SEQUENCE: 28
acgagcgtct ggccagcagc tcggagctcc tctgcgcgcg gcgggctggc agcgggcccg      60
aggcgagcgg gacagattga ctggaagccg agagtccagg cggcagcggg aattgacagg     120
aggactacgc cgcaagggat aggcccagaa tagcaaccag gaaacaaaat ctcatcatgg     180
ccaatgtcca ccaggaaaac gaaagagctgg agcagcccct gcagaatgga caggaagacc     240
gccctgtggg aggaggtgag ggccaccagc ctgctgcaaa caacaacaac aacaaccaca     300
accataacca caaccaccac cgaagaggcc aggctcgccg acttgcccct aacttccgat     360
gggccattcc caacaggcag atgaatgacg ggttgggtgg agatggagat gatatggaaa     420
tgttcatgga ggagatgaga gagatccgga gaaagcttag ggagctacag ctgagaaatt     480
gtctacgcat ccttatgggg gagctgtcta accaccacga tcaccatgat gaattctgcc     540
ttatgccttg acttcggtca ttccccctg agatccatac tgtgactccc gctgtagccc      600
tttcctcgc attttcctga catgccttta atgacccgtt tgtggtgagc cttgtgttat      660
ttccatgcca tgtgccaggt ggggcttgtg ttgccagtga                            700

<210> SEQ ID NO 29
<211> LENGTH: 891
<212> TYPE: DNA
<213> ORGANISM: Human

<400> SEQUENCE: 29
accccatccc ccactcctat accggtcctc cattttggtg cctgcaaagc tctgggaaag      60
```

-continued

```
aatcccggga acgaaaaat ggtgggtttg ggggaaggga ggtaagggga gaaagctgga    120 gggagggct ttaattggag gccccgtaga ggacgcgcgg aacttctaag gtgggaaaaa    180
acgaaattaa aaaatccttt gatatcaggg ctctgaatcc tgctggtcag agcaccaagc    240
attcagtctc tctccttgcc tttgtcttac ttgtgttcaa agaaaaacaa ccagaaaaaa    300
aaaatctcat catggcaaat attcaccagg aaaacgaaga gatggagcag cctatgcaga    360
atggagagga agaccgccct tgggaggag gtgaaggcca ccagcctgca ggaaatcgac    420
ggggacaggc tcgccgactt gccctaatt ttcgatgggc ataccccaat aggcagatca    480
atgatgggat gggtggagat ggagatgata tggaaatatt catggaggag atgagagaaa    540
tcagaagaaa acttagggag ctgcagttga ggaattgtct gcgtatcctt atgggggagc    600
tctctaatca ccatgaccat catgatgaat tttgccttat gccttgactc ctgccattta    660
tcatgagatt aatactgtga ttcccgctgt tttctttttc cttgcatttt cctaatatgc    720
ctttactgat ccgtttgctg tgaaccctat gttatttcca tgtgtcaagt gggtcttgtg    780
ttgccagctt ctatttgaag attgcctttg cactcagtgt aagtttctgt cagcagtagt    840
ttcacccatt tgcatggaaa aatttaaagc taataaagca atttaaaaag c            891
```

<210> SEQ ID NO 30
<211> LENGTH: 128
<212> TYPE: PRT
<213> ORGANISM: Mouse

<400> SEQUENCE: 30

Met Glu Ser Lys Asp Gln Gly Val Lys Asn Leu Asn Met Glu Asn Asp
1               5                   10                  15

His Gln Lys Lys Glu Glu Lys Glu Glu Lys Pro Gln Asp Thr Ile Arg
            20                  25                  30

Arg Glu Pro Ala Val Ala Leu Ile Ser Glu Ala Gly Lys Asn Cys Ala
        35                  40                  45

Pro Arg Gly Gly Arg Arg Phe Arg Val Arg Gln Pro Ile Ala His
    50                  55                  60

Tyr Arg Trp Asp Leu Met Gln Arg Val Gly Glu Pro Gln Gly Arg Met
65                  70                  75                  80

Arg Glu Glu Asn Val Gln Arg Phe Gly Gly Asp Val Arg Gln Leu Met
                85                  90                  95

Glu Lys Leu Arg Glu Arg Gln Leu Ser His Ser Leu Arg Ala Val Ser
            100                 105                 110

Thr Asp Pro Pro His His Asp His His Asp Glu Phe Cys Leu Met Pro
        115                 120                 125

<210> SEQ ID NO 31
<211> LENGTH: 128
<212> TYPE: PRT
<213> ORGANISM: Mouse

<400> SEQUENCE: 31

Met Glu Ser Lys Glu Glu Arg Ala Leu Asn Asn Leu Ile Val Glu Asn
1               5                   10                  15

Val Asn Gln Glu Asn Asp Glu Lys Asp Glu Lys Glu Gln Val Ala Asn
            20                  25                  30

Lys Gly Glu Pro Leu Ala Leu Pro Leu Asn Val Ser Glu Tyr Cys Val
        35                  40                  45

Pro Arg Gly Asn Arg Arg Arg Phe Arg Val Arg Gln Pro Ile Leu Gln

-continued

```
                50                  55                  60
Tyr Arg Trp Asp Ile Met His Arg Leu Gly Glu Pro Gln Ala Arg Met
 65                  70                  75                  80

Arg Glu Glu Asn Met Glu Arg Ile Gly Glu Val Arg Gln Leu Met
                 85                  90                  95

Glu Lys Leu Arg Glu Lys Gln Leu Ser His Ser Leu Arg Ala Val Ser
                100                 105                 110

Thr Asp Pro Pro His His Asp His Asp Glu Phe Cys Leu Met Pro
                115                 120                 125
```

<210> SEQ ID NO 32
<211> LENGTH: 125
<212> TYPE: PRT
<213> ORGANISM: Mouse

<400> SEQUENCE: 32

```
Met Glu Ser Lys Glu Lys Arg Ala Val Asn Ser Leu Ser Met Glu Asn
 1               5                  10                  15

Ala Asn Gln Glu Asn Glu Glu Lys Glu Gln Val Ala Asn Lys Gly Glu
                20                  25                  30

Pro Leu Ala Leu Pro Leu Asp Ala Gly Glu Tyr Cys Val Pro Arg Gly
                35                  40                  45

Asn Arg Arg Arg Phe Pro Val Arg Gln Pro Ile Leu Gln Tyr Arg Trp
 50                  55                  60

Asp Ile Met His Arg Leu Gly Glu Pro Gln Ala Arg Met Arg Glu Glu
 65                  70                  75                  80

Asn Met Glu Arg Ile Gly Glu Glu Val Arg Gln Leu Met Glu Lys Leu
                 85                  90                  95

Arg Glu Lys Gln Leu Ser His Ser Leu Arg Ala Val Ser Thr Asp Pro
                100                 105                 110

Pro His His Asp His His Asp Glu Phe Cys Leu Met Pro
                115                 120                 125
```

<210> SEQ ID NO 33
<211> LENGTH: 128
<212> TYPE: PRT
<213> ORGANISM: Mouse

<400> SEQUENCE: 33

```
Met Glu Ser Lys Asp Gln Gly Ala Lys Asn Leu Asn Met Glu Asn Asp
 1               5                  10                  15

His Gln Lys Lys Glu Glu Lys Glu Glu Lys Pro Gln Asp Thr Ile Lys
                20                  25                  30

Arg Glu Pro Val Val Ala Pro Thr Phe Glu Ala Gly Lys Asn Cys Ala
                35                  40                  45

Pro Arg Gly Gly Arg Arg Phe Arg Val Arg Gln Pro Ile Ser His
 50                  55                  60

Tyr Arg Trp Asp Leu Met His Arg Val Gly Glu Pro Gln Gly Arg Met
 65                  70                  75                  80

Arg Glu Glu Asn Val Gln Arg Phe Gly Glu Asp Met Arg Gln Leu Met
                 85                  90                  95

Glu Lys Leu Arg Glu Arg Gln Leu Ser His Ser Leu Arg Ala Val Ser
                100                 105                 110

Thr Asp Pro Pro His His Asp His Asp Glu Phe Cys Leu Met Pro
                115                 120                 125
```

```
<210> SEQ ID NO 34
<211> LENGTH: 118
<212> TYPE: PRT
<213> ORGANISM: Mouse

<400> SEQUENCE: 34

Met Ala Ser Lys Val Lys Gln Val Ile Leu Asp Leu Thr Val Glu Lys
1               5                   10                  15

Asp Lys Lys Asn Lys Lys Gly Gly Lys Ala Ser Lys Gln Ser Glu Glu
            20                  25                  30

Glu Ser His His Leu Glu Glu Val Glu Asn Lys Lys Pro Gly Gly Asn
        35                  40                  45

Val Arg Arg Lys Val Arg Arg Leu Val Pro Asn Phe Leu Trp Ala Ile
    50                  55                  60

Pro Asn Arg His Val Asp His Ser Glu Gly Glu Glu Val Gly Arg
65                  70                  75                  80

Phe Val Gly Gln Val Met Glu Ala Lys Arg Lys Ser Lys Glu Gln Gln
                85                  90                  95

Met Arg Pro Tyr Thr Arg Phe Arg Thr Pro Glu Pro Asp Asn His Tyr
            100                 105                 110

Asp Phe Cys Leu Ile Pro
            115

<210> SEQ ID NO 35
<211> LENGTH: 118
<212> TYPE: PRT
<213> ORGANISM: Mouse

<400> SEQUENCE: 35

Met Ala Ser Lys Phe Lys Gln Val Ile Leu Asp Leu Thr Val Glu Lys
1               5                   10                  15

Asp Lys Lys Asp Lys Arg Gly Gly Lys Ala Ser Lys Gln Ser Glu Glu
            20                  25                  30

Glu Pro His His Leu Glu Glu Val Glu Asn Lys Lys Pro Gly Gly Asn
        35                  40                  45

Val Arg Arg Lys Val Arg Arg Leu Val Pro Asn Phe Leu Trp Ala Ile
    50                  55                  60

Pro Asn Arg His Val Asp Arg Asn Glu Gly Gly Glu Asp Val Gly Arg
65                  70                  75                  80

Phe Val Val Gln Gly Thr Glu Val Lys Arg Lys Thr Thr Glu Gln Gln
                85                  90                  95

Val Arg Pro Tyr Arg Arg Phe Arg Thr Pro Glu Pro Asp Asn His Tyr
            100                 105                 110

Asp Phe Cys Leu Ile Pro
            115

<210> SEQ ID NO 36
<211> LENGTH: 111
<212> TYPE: PRT
<213> ORGANISM: Mouse

<400> SEQUENCE: 36

Met Ala Asn Ile His Gln Glu Asn Glu Glu Met Glu Gln Pro Met Gln
1               5                   10                  15

Asn Gly Glu Glu Asp Arg Pro Leu Gly Gly Glu Gly His Gln Pro
            20                  25                  30

Ala Gly Asn Arg Arg Gly Gln Ala Arg Arg Leu Ala Pro Asn Phe Arg
        35                  40                  45
```

```
Trp Ala Ile Pro Asn Arg Gln Ile Asn Asp Gly Met Gly Gly Asp Gly
         50                  55                  60

Asp Asp Met Glu Ile Phe Met Glu Glu Met Arg Glu Ile Arg Arg Lys
 65                  70                  75                  80

Leu Arg Glu Leu Gln Leu Arg Asn Cys Leu Arg Ile Leu Met Gly Glu
                 85                  90                  95

Leu Ser Asn His His Asp His His Asp Glu Phe Cys Leu Met Pro
             100                 105                 110
```

<210> SEQ ID NO 37
<211> LENGTH: 120
<212> TYPE: PRT
<213> ORGANISM: Mouse

<400> SEQUENCE: 37

```
Met Glu Gln Pro Leu Gln Asn Gly Gln Glu Asp Arg Pro Val Gly Gly
 1               5                  10                  15

Gly Glu Gly His Gln Pro Ala Ala Asn Asn Asn His Asn His Asn
                 20                  25                  30

His Asn His Asn His Ser His Asn His Asn His His Arg Arg Gly Gln
             35                  40                  45

Ala Arg Arg Leu Ala Pro Asn Phe Arg Trp Ala Ile Pro Asn Arg Gln
         50                  55                  60

Met Asn Asp Gly Leu Gly Gly Asp Gly Asp Asp Met Glu Met Phe Met
 65                  70                  75                  80

Glu Glu Met Arg Glu Ile Arg Arg Lys Leu Arg Glu Leu Gln Leu Arg
                 85                  90                  95

Asn Cys Leu Arg Ile Leu Met Gly Glu Leu Ser Asn His His Asp His
             100                 105                 110

His Asp Glu Phe Cys Leu Met Pro
         115                 120
```

<210> SEQ ID NO 38
<211> LENGTH: 120
<212> TYPE: PRT
<213> ORGANISM: Mouse

<400> SEQUENCE: 38

```
Met Glu Gln Pro Leu Gln Asn Gly Gln Glu Asp Arg Pro Val Gly Gly
 1               5                  10                  15

Gly Glu Gly His Gln Pro Ala Ala Asn Asn Asn His Asn His Asn
                 20                  25                  30

His Asn His Asn His Ser His Asn His Asn His His Arg Arg Gly Gln
             35                  40                  45

Ala Arg Arg Leu Ala Pro Asn Phe Arg Trp Ala Ile Pro Asn Arg Gln
         50                  55                  60

Met Asn Asp Gly Leu Gly Gly Asp Gly Asp Asp Met Glu Met Phe Met
 65                  70                  75                  80

Glu Glu Met Arg Glu Ile Arg Arg Lys Leu Arg Glu Leu Gln Leu Arg
                 85                  90                  95

Asn Cys Leu Arg Ile Leu Met Gly Glu Leu Ser Asn His His Asp His
             100                 105                 110

His Asp Glu Phe Cys Leu Met Pro
         115                 120
```

<210> SEQ ID NO 39

```
<211> LENGTH: 111
<212> TYPE: PRT
<213> ORGANISM: Mouse

<400> SEQUENCE: 39

Met Glu Asn Val Pro Lys Glu Asn Lys Val Glu Lys Ala Pro Val
1               5                   10                  15

Gln Asn Glu Ala Pro Ala Leu Gly Gly Gly Glu Tyr Gln Glu Pro Gly
            20                  25                  30

Gly Asn Val Lys Gly Val Trp Ala Pro Ala Pro Gly Phe Gly Glu
        35                  40                  45

Asp Val Pro Asn Arg Leu Val Asp Asn Ile Asp Met Ile Asp Gly Asp
    50                  55                  60

Gly Asp Asp Met Glu Arg Phe Met Glu Glu Met Arg Glu Leu Arg Arg
65                  70                  75                  80

Lys Ile Arg Glu Leu Gln Leu Arg Tyr Ser Leu Arg Ile Leu Ile Gly
                85                  90                  95

Asp Pro Pro His His Asp His His Asp Glu Phe Cys Leu Met Pro
                100                 105                 110

<210> SEQ ID NO 40
<211> LENGTH: 13
<212> TYPE: PRT
<213> ORGANISM: Mouse

<400> SEQUENCE: 40

Arg Glu Ile Arg Arg Lys Leu Arg Glu Leu Gln Leu Arg
1               5                   10

<210> SEQ ID NO 41
<211> LENGTH: 13
<212> TYPE: PRT
<213> ORGANISM: Human

<400> SEQUENCE: 41

Arg Glu Ile Arg Arg Lys Leu Arg Glu Leu Gln Leu Arg
1               5                   10

<210> SEQ ID NO 42
<211> LENGTH: 10
<212> TYPE: PRT
<213> ORGANISM: Mouse

<400> SEQUENCE: 42

Leu Pro Pro Leu Glu Arg Leu Thr Leu Asp
1               5                   10

<210> SEQ ID NO 43
<211> LENGTH: 12
<212> TYPE: PRT
<213> ORGANISM: Mouse

<400> SEQUENCE: 43

Ala Leu Gln Lys Lys Leu Glu Glu Leu Glu Leu Asp
1               5                   10

<210> SEQ ID NO 44
<211> LENGTH: 12
<212> TYPE: PRT
<213> ORGANISM: Mouse

<400> SEQUENCE: 44
```

-continued

```
Leu Thr Met Lys Glu Val Glu Leu Glu Leu Leu
1               5                   10
```

<210> SEQ ID NO 45
<211> LENGTH: 10
<212> TYPE: PRT
<213> ORGANISM: Mouse

<400> SEQUENCE: 45

```
Leu Ala Leu Lys Leu Ala Gly Leu Asp Ile
1               5                   10
```